(12) United States Patent
Hochman

(10) Patent No.: US 6,495,601 B1
(45) Date of Patent: Dec. 17, 2002

(54) METHODS AND COMPOSITIONS FOR TREATING CONDITIONS OF THE CENTRAL AND PERIPHERAL NERVOUS SYSTEMS USING NON-SYNAPTIC MECHANISMS

(75) Inventor: Daryl W. Hochman, Seattle, WA (US)

(73) Assignee: Cytoscan Sciences LLC, Seattle, WA (US)

( * ) Notice: Subject to any disclaimer, the term of this patent is extended or adjusted under 35 U.S.C. 154(b) by 0 days.

(21) Appl. No.: 09/470,637

(22) Filed: Dec. 22, 1999

Related U.S. Application Data

(60) Provisional application No. 60/113,620, filed on Dec. 23, 1998.

(51) Int. Cl.$^7$ ............... A61K 31/195; A61K 31/18; A61K 31/505
(52) U.S. Cl. ............ 514/562; 514/603; 514/269
(58) Field of Search ............... 514/603, 562, 514/269; 435/29

(56) References Cited

U.S. PATENT DOCUMENTS

| | | | |
|---|---|---|---|
| 3,676,454 A | 7/1972 | Vida | 260/309.5 |
| 5,486,530 A | 1/1996 | Boelke et al. | 514/347 |
| 5,498,519 A | 3/1996 | Rubin et al. | 435/1.2 |
| 5,571,842 A | 11/1996 | Kleemann et al. | 514/618 |
| 5,585,401 A | 12/1996 | Brandt et al. | 514/562 |
| 5,658,786 A | * 8/1997 | Smith et al. | 435/365 |
| 5,834,466 A | 11/1998 | Ramasamy et al. | 514/227.5 |
| 5,902,732 A | 5/1999 | Hochman | 435/29 |
| 5,976,825 A | 11/1999 | Hochman | 435/29 |

OTHER PUBLICATIONS

"Treatment of Convulsive Ecalmpsia Crisis by Therapeutic Combination; Diazepam, Dihydralazine, Furosemide", 1971, Ngohou–Bonevat et al, Bulletin De La Federation Des Societes De Gynecologie et a D Obstertrique De Langue Francaise.*

"Treatment of Hyponatraemic Seizures with Intravenos 29.2% Saline", Worthley et al, 1989, Br. Med. J, vol. 292, pp 168–170.*

"Volumne–sensitive release of taurine from cultured astrocytes: properties and mechanism", Pasantes–Morales et al., 1990, Glia, 3(5), 427–32, Abstract.*

Hesdorffer, D.C., et al., "Severe, Uncontrolled Hypertension and Adult–Onset Seizures: A Case–Control Study in Rochester, Minnesota," *Epilepsia*, vol. 37, No. 8, pp. 736–741 (1996).

Hochman, Daryl W., et al., "Dissociation of Synchronization and Excitability in Furosemide Blockade of Epileptiform Activity," *Science*, vol. 270, pp. 99–102 (Oct. 6, 1995).

Snow, Robert W., et al., "Electrophysiological and Optical Changes in Slice of Rat Hippocampus During Spreading Depression," *Journal of Neurophysiology*, vol. 50, No. 3, pp. 561–572 (Sep. 1983).

Brazil, Carl W., et al., "Advances in the Medical Treatment of Epilepsy," *Annu. Rev. Med.*, vol. 49, pp. 135–162 (1998).

Parsons, Andrew A., "Recent Advances in Mechanisms of Spreading Depression," *Current Opinion in Neurology*, vol. 11, pp. 227–231 (1998).

Jaffreys, John G.R., "Mechanisms and Experimental Models of Seizure Generation," *Current Opinion in Neurology*, vol. 11, pp. 123–127 (1998).

Hochman, Daryl W., Ph.C., "Intrinsic Optical Changes in Neuronal Tissue," *Neurosurgery Clinics of North America*, vol. 8, No. 3, pp. 393–412 (Jul. 1997).

Haglund, Michael M., M.D., Ph.D., et al., "Enhanced Optical Imaging of Human Gliomas and Tumor Margins," *Neurosurgery*, vol. 38, No. 2, pp. 308–317 (Feb. 1996).

Haglund, Michael M., M.D., Ph.D., et al., "Enhanced Optical Imaging of Rat Gliomas and Tumor Margins," *Neurosurgery*, vol. 35, No. 5, pp. 930–941 (Nov. 1994).

Collins, Michael A., et al., "Brain Damage Due to Episodic Alcohol Exposure In Vivo and In Vitro: Furosemide Neuroprotection Implicates Edema–Based Mechanism," *The FASEB Journal*, vol. 12, pp. 221–230 (Feb. 1998).

Haglund, Michael M., et al., "Optical Imaging of Epileptiform and Functional Activity in Human Cerebral Cortex," *Nature*, vol. 358, pp. 668–671 (Aug. 1992).

(List continued on next page.)

*Primary Examiner*—Zohreh Fay
*Assistant Examiner*—Brian Yong S Kwon
(74) *Attorney, Agent, or Firm*—Ann W. Speakman; Susan J. Friedman

(57) ABSTRACT

The present invention relates to methods and compositions for treating selected conditions of the central and peripheral nervous systems employing non-synaptic mechanisms. More specifically, one aspect of the present invention relates to methods and materials for treating seizure and seizure disorders, epilepsy, status epilepticus, migraine, spreading depression, intracranial hypertension; for treating the pathophysiological effects of head trauma, stroke, ischemia and hypoxia; for treating or protecting from the pathophysiological effects of neurotoxic agents such as ethanol; and for treating neurophsyciatric disorders and central nervous system edema by administering agents that modulate ionic concentrations and/or ionic gradients in the brain, particularly ion-dependent or cation-chloride cotransporter antagonists. Ion-dependent cotransport antagonists and combinations of such compositions with other agents for treating various conditions are disclosed. The present invention also relates to methods and compositions for treating pain by administering ion-dependent cotransporter antagonists. Methods and compositions for enhancing cortical function, for example, in centers of cognition, learning and memory, by administering ion-dependent cotransporter agonists are disclosed. Methods and systems for screening drug candidate compounds for desired activities using in vitro and in vivo systems are disclosed.

6 Claims, 8 Drawing Sheets

OTHER PUBLICATIONS

Mathew, Ninan T., M.D., et al., "Coexistence of Migraine and Idiopathic Intracranial Hypertension Without Papilledema," *Neurology,* vol. 46, pp. 1226–1230 (May 1996).

Read, S.J., et al., "Furosemide Inhibits Regenerative Cortical Spreading Depression in Anaesthetized Cats," *Cephalalgia,* vol. 17, pp. 826–832 (1997).

Schwartzkroin, Philip A., et al., "Osmolarity, Ionic Flux, and Changes in Brain Excitability," *Epilepsy Research,* vol. 32, pp. 275–285 (1998).

Carter, C.H., "Status Epilepticus Treated by Intravenous Urea," *Epilepsia,* vol. 3, pp. 198–200 (1962).

Reed, Donal J., et al., "The Effect of Hypertonic Urea Solution on Electroshock Seizure Threshold and Eletrolyte Distribution in Rats," *Reed and Woodbury,* vol. 146, pp. 154–159 (1964).

Lowenstein, Daniel H., M.D., et al., "Status Epilepticus," *The New England Journal of Medicine,* vol. 338, No. 14, pp. 970–976 (Apr. 2, 1998).

Upton, Neil, "Mechanisms of Action of New Antiepileptic Drugs: Rational Design and Serendipitous Findings," *TiPS,* vol. 15, pp. 456–463 (Dec. 1994).

Macdonald, Robert L., et al., "Mechanisms of Action of New Antiepileptic Drugs," *Current Opinion in Neurology,* vol. 10, pp. 121–128 (1997).

Welch, K.M.A., M.D., "Pathogenesis of Migraine," *Seminars in Neurology,* vol. 17, No. 4, pp. 335–341 (1997).

Welch, K.M.A., M.D., "Current Opinions in Headache Pathogenesis: Introduction and Synthesis," *Current Opinion in Neurology,* vol. 11, pp. 193–197 (1998).

McLeod, M.S., "The Mysterious Etiology of Head Pain," *Medical Sciences Bulletin,* (Jul. 1996).

Welch, Mike, M.D., "Brain Imaging Studies Support Neuroelectric Etiology of Migraine Aura," *Reuters Health Information,* 2 pages (May 10, 1999)—Abstract.

Welch, K.M., et al., "The Concept of Migraine as a State of Central Neuronal Hyperexcitability," *Neural Clin.,* vol. 8, pp. 817–828 (1990)—Abstract.

Diener, H.C., et al., "Emerging Treatments in Headache," *European Neurology,* vol. 38, No. 3, pp. 167–174 (1997)—Abstract.

Rivera, C., et al., "The $K^+/Cl^-$ Co–Transporter KCC2 Renders GABA Hyperpolarizing During Neuronal Maturation," *Nature,* vol. 397, No. 6716, pp. 251–255 (Jan. 21, 1999)—Abstract.

Lambert, G.A., et al., "Cortical Spreading Depression Reduces Dural Blood Flow—A Possiboe Mechanism for Migraine Pain?" *Cephalagia,* vol. 14., No. 6, pp. 430–436 (Dec. 1994).

Obrenovitch, T.P., et al., "Inhibition of Cortical Spreading Depression by L–701, 324, A Novel Antagonist at the Glycine Site of the N–Methyl–D–Aspartate Receptor Complex." *British Journal of Pharmacology,* vol. 117., No. 5, pp. 931–937 (Mar. 1997).

Welch, K.M.A., M.D., "Cortical Hyperexcitability Seen As Mechanism for Migraine With Aura," *Reuters Health Information Bulletin,* Jun. 20, 1997.

* cited by examiner

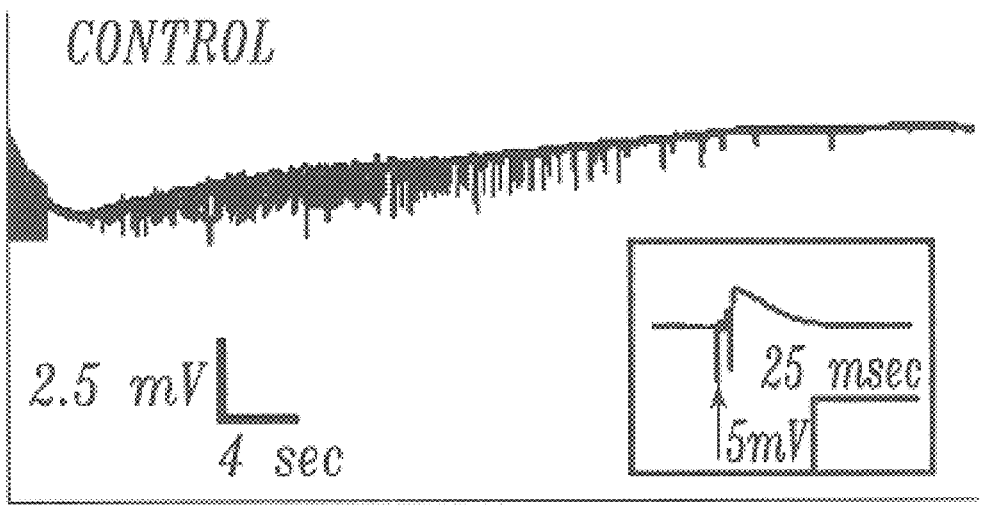
Fig. 1A
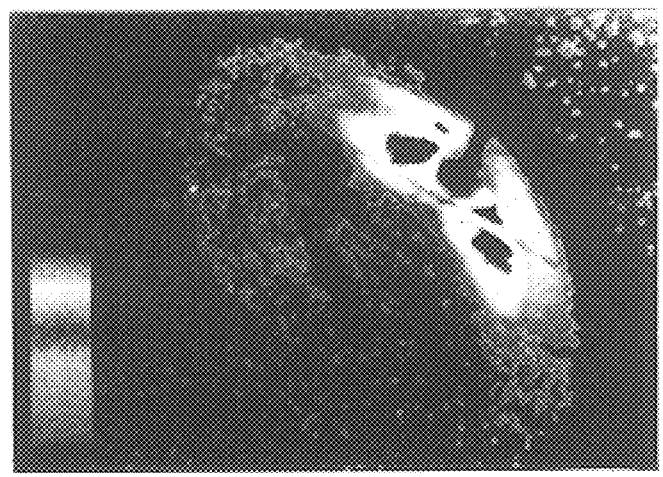
Fig. 1A1

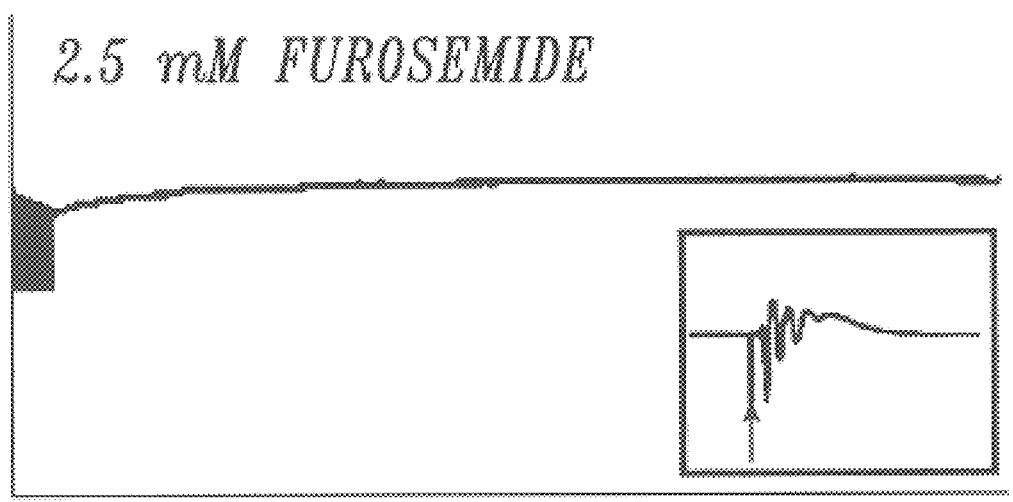
Fig. 1B
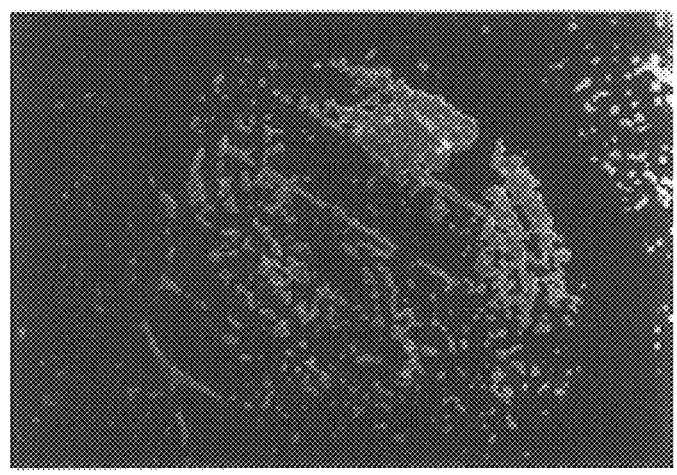
Fig. 1B1

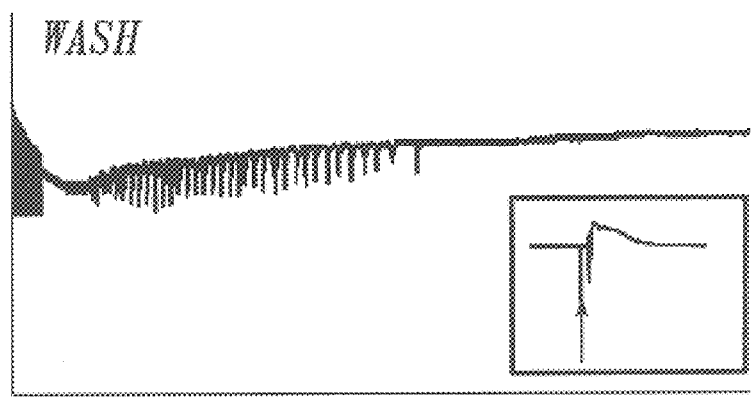
Fig. 1C
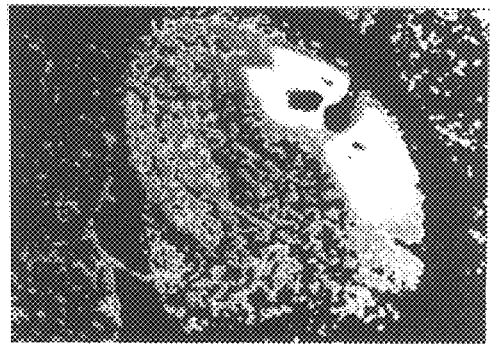
Fig. 1C1
Fig. 1D 2 s / 1 mV 2 s / 1 mV 2 s / 1 mV 10 s / 5 mV

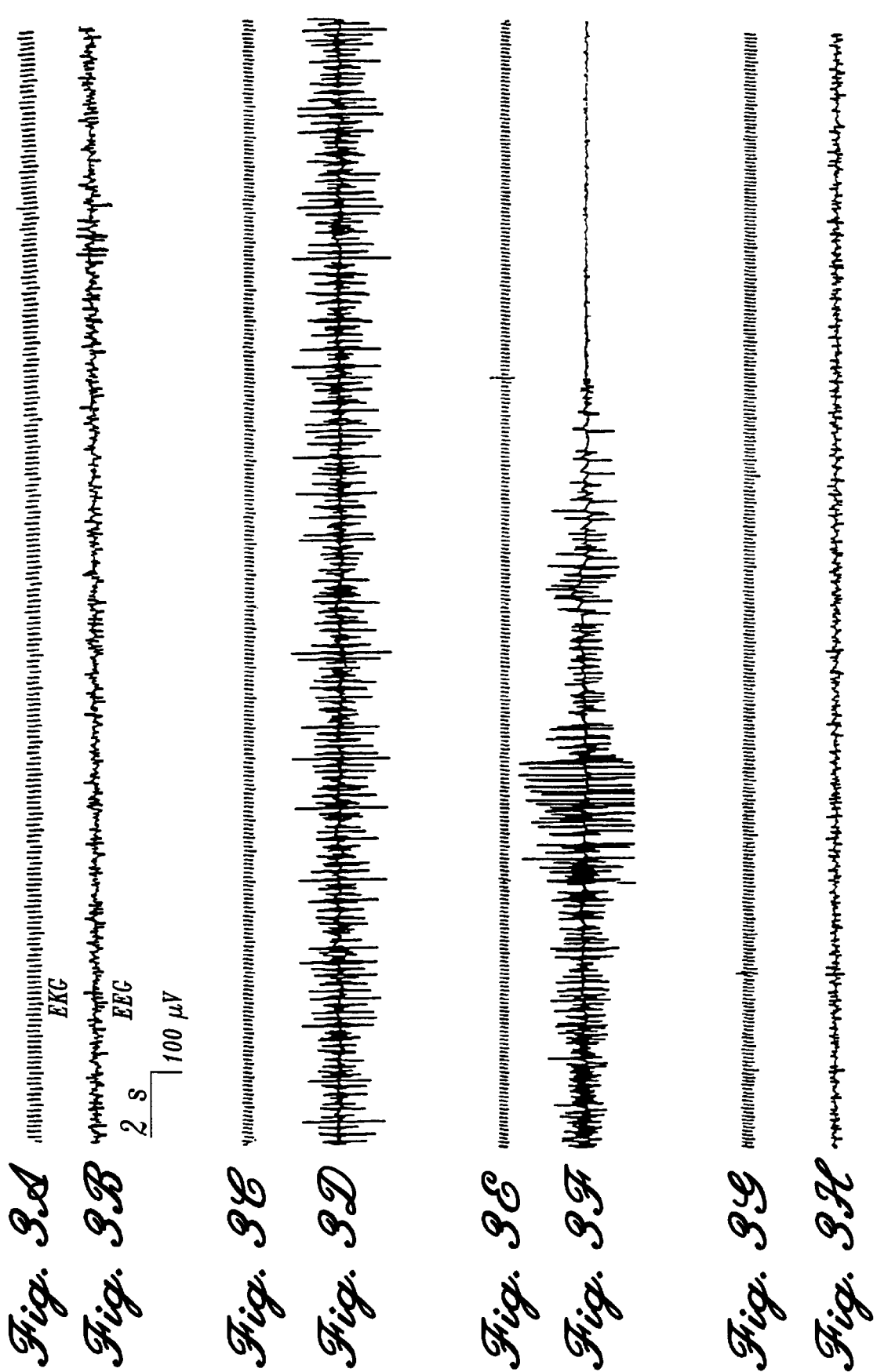

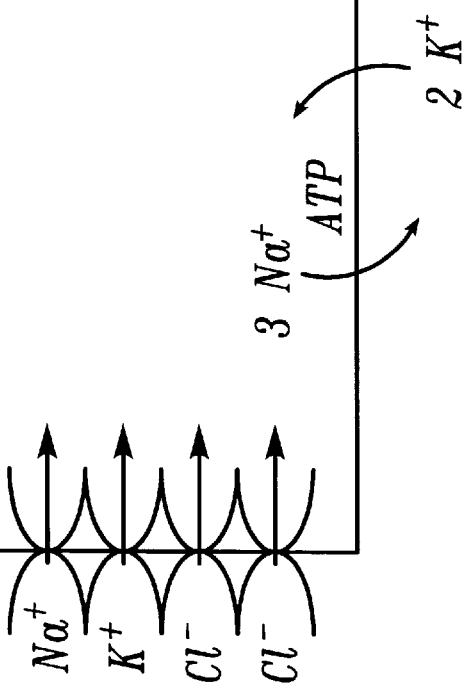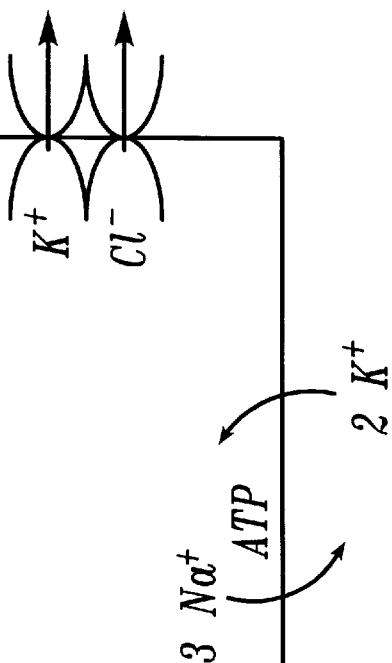
Fig. 4A

METHODS AND COMPOSITIONS FOR TREATING CONDITIONS OF THE CENTRAL AND PERIPHERAL NERVOUS SYSTEMS USING NON-SYNAPTIC MECHANISMS

REFERENCE TO PRIORITY APPLICATION

This application claims priority to U.S. patent application No. 60/113,620, filed Dec. 23, 1998.

TECHNICAL FIELD OF THE INVENTION

The present invention relates to methods and compositions for treating selected conditions of the central and peripheral nervous systems employing non-synaptic mechanisms. More specifically, one aspect of the present invention relates to methods and materials for treating seizures and seizure disorders, epilepsy, status epilepticus, migraine headache, cortical spreading depression, intracranial hypertension, neuropsychiatric disorders, central nervous system edema; for treating or protecting from the pathophysiological effects of toxic agents such as ethanol and certain infectious agents; for treating the pathophysiological effects of head trauma, stroke, ischemia and hypoxia; and for improving certain brain functions, such as cognition, learning and memory by administering agents that modulate ionic concentrations and ionic balances in the central nervous system. Specific treatment compositions, including loop diuretics, analogs and derivatives of such compositions, as well as combinations of such compositions with other agents for modulating ionic concentrations and gradients, and for treating various conditions, are disclosed. Materials and methods for treating pain by administering agents that modulate ionic concentrations and gradients in the peripheral nervous system are also disclosed. Methods and systems for screening drug candidate compounds for desired activities using in vitro and in vivo systems are described.

BACKGROUND OF THE INVENTION

Conventional treatments for neuronal disorders, such as seizure disorders, epilepsy, and the like, target synaptic mechanisms that affect excitatory pathways, such as by modulating the release or activity of neurotransmitters or inhibitors. Conventional treatment agents and regimen for seizure disorders diminish neuronal excitability and inhibit synaptic firing. One serious drawback of this approach is that while seizures are generally localized, the treatment affects (diminishes) neuronal activity indiscriminately. For this reason, there are serious side effects and repeated use of conventional medications may result in unintended deficiencies in normal and desirable brain functions, such as cognition, learning and memory. More detailed information concerning particular disorders of interest is provided below.

Epilepsy

Epilepsy is characterized by abnormal discharges of cerebral neurons and typically manifested as various types of seizures. Epileptiform activity is identified with spontaneously occurring synchronized discharges of neuronal populations that can be measured using electrophysiological techniques. This synchronized activity, which distinguishes epileptiform from non-epileptiform activity, is referred to as "hypersynchronization" because it describes the state in which individual neurons become increasingly likely to discharge in a time-locked manner with one another.

Epilepsy is one of the most common neurological disorders, affecting about 1% of the population. There are various forms of epilepsy, including idiopathic, symptomatic and cryptogenic. Genetic predisposition is thought to be the predominant etiologic factor in idiopathic epilepsy. Symptomatic epilepsy usually develops as a result of a structural abnormality in the brain.

Status epilepticus is a particularly severe form of seizure, which is manifested as multiple seizures that persist for a significant length of time, or serial seizures without any recovery of consciousness between seizures. The overall mortality rate among adults with status epilepticus is approximately 20 percent. Patients who have a first episode are at substantial risk for future episodes and the development of chronic epilepsy. The frequency of status epilepticus in the United States is approximately 150,000 cases per year, and roughly 55,000 deaths are associated with status epilepticus annually. Acute processes that are associated with status epilepticus include intractable epilepsy, metabolic disturbances (e.g. electrolyte abnormalities, renal failure and sepsis), central nervous system infection (meningitis or encephalitis), stroke, degenerative diseases, head trauma, drug toxicity and hypoxia. The fundamental pathophysiology of status epilepticus involves a failure of mechanisms that normally abort an isolated seizure. This failure can arise from abnormally persistent, excessive excitation or ineffective recruitment of inhibition. Studies have shown that excessive activation of excitatory amino acid receptors can cause prolonged seizures and suggest that excitatory amino acids may play a causative role. Status epilepticus can also be caused by penicillin and related compounds that antagonize the effects of γ-aminobutyric acid (GABA), the primary inhibitory neurotransmitter in the brain.

One early diagnostic procedure for epilepsy involved the oral administration of large quantities of water together with injections of vasopressin to prevent the accompanying diuresis. This treatment was found to induce seizures in epileptic patients, but rarely in non-epileptic individuals (Garland et al., *Lancet*, 2:566, 1943). Status epilepticus can be blocked in kainic acid-treated rats by intravenous injection of mannitol (Baran et al., *Neuroscience*, 21:679, 1987). This effect is similar to that achieved by intravenous injection of urea in human patients (Carter, *Epilepsia*, 3:198, 1962). The treatment in each of these cases increases the osmolarity of the blood and extracellular fluid, resulting in water efflux from the cells and an increase in extracellular space in the brain. Acetazolamide (ACZ), another diuretic with a different mechanism of action (inhibition of carbonic anhydrase), has been studied experimentally as an anticonvulsant (White et al., *Advance Neurol.*, 44:695, 1986; and Guillaume et al., *Epilepsia*, 32:10, 1991) and used clinically on a limited basis (Tanimukai et al., *Biochem. Pharm.*, 14:961, 1965; and Forsythe et al., *Develop. Med. Child Neurol.*, 23:761, 1981). Although its mechanism of anticonvulsant action has not been determined, ACZ does have a clear effect on the cerebral extracellular space.

Traditional anti-epileptic drugs exert their principal effect through one of three mechanisms: (a) inhibition of repetitive, high-frequency neuronal firing by blocking voltage-dependent sodium channels; (b) potentiation of γ-aminobutyric acid (GABA)-mediated postsynaptic inhibition; and (c) blockade of T-type calcium channels. Phenytoin and carbamazepine are examples of sodium channel antagonists, which exert their effect at the cellular level by reducing or eliminating sustained high-frequency neuronal depolarization while not appreciably affecting regular firing rates of neurons. Barbiturates, such as Phenobarbital and benzodiazepines, act by enhancing GABA-mediated synaptic inhibition. Both classes of compounds increase the hyperpolarization of the postsynaptic membrane, resulting in increased inhibition. Ethosuximide and valporate are examples of drugs that decrease calcium entry into neurons through T-type voltage-dependent calcium channels.

Current anti-epileptic drug therapies exert their pharmacological effects on all brain cells, regardless of their involvement in seizure activity. Common side effects are over-sedation, dizziness, loss of memory and liver damage. Additionally, 20–30% of epilepsy patients are refractory to current therapy.

Focus on synaptic hyperexcitability has been a guiding principle in basic research on the mechanisms of epileptogenesis and in the design and discovery of new anti-epileptic drugs. One of the shortcomings of this approach is that most current anti-epilepsy drugs exert their influence in an indiscriminate manner, in both the epileptogenic and normal areas in the brain. The compositions of the present invention offer a novel approach to the treatment of seizures, in part because they act via a non-synaptic pathway.

Migraine

Migraine headaches afflict 10–20% of the U.S. population, with an estimated loss of 64 million workdays annually. Migraine headache is characterized by pulsating head pain that is episodic, unilateral or bilateral, lasting from 4 to 72 hours and often associated with nausea, vomiting and hypersensitivity to light and/or sound. When accompanied by premonitory symptoms, such as visual, sensory, speech or motor symptoms, the headache is referred to as "migraine with aura," formerly known as classic migraine. When not accompanied by such symptoms, the headache is referred to as "migraine without aura," formerly known as common migraine. Both types evidence a strong genetic component, and both are three times more common in women than men. The precise etiology of migraine has yet to be determined. It is theorized that persons prone to migraine have a reduced threshold for neuronal excitability, possibly due to reduced activity of the inhibitory neurotransmitter γ-aminobutyric acid (GABA). GABA normally inhibits the activity of the neurotransmitters serotonin (5-HT) and glutamate, both of which appear to be involved in migraine attacks. The excitatory neurotransmitter glutamate is implicated in an electrical phenomenon called cortical spreading depression, which can initiate a migraine attack, while serotonin is implicated in vascular changes that occur as the migraine progresses.

Cortical spreading depression (CSD) is characterized by a short burst of intense depolarization in the occipital cortex, followed by a wave of neuronal silence and diminished evoked potentials that advance anteriorly across the surface of the cerebral cortex. Enhanced excitability of the occipital-cortex neurons has been proposed as the basis for CSD. The visual cortex may have a lower threshold for excitability and therefore is most prone to CSD. Mitochondrial disorders, magnesium deficiency and abnormality of presynaptic calcium channels may be responsible for neuronal hyperexcitability (Welch, K. M. A., Pathogenesis of Migraine, *Seminars in Neurobiology*, vol. 17:4, 1997). During a spreading depression event, profound ionic perturbations occur, which include interstitial acidification, extracellular potassium accumulation and redistribution of sodium and chloride ions to intracellular compartments. In addition, prolonged glial swelling occurs as a homeostatic response to altered ionic extracellular fluid composition and interstitial neurotransmitter and fatty acid accumulation. Studies have shown that furosemide inhibits regenerative cortical spreading depression in anaesthetized cats (Read, S J, et al, *Cephalagia*, 17:826, 1997).

A study of eighty-five patients with refractory transformed migraine type of chronic daily headache (CDH) concluded that acute headache exacerbations responded to specific anti-migraine agents such as ergotamine, dihydroergotamine (DHE), and sumatriptan, and addition of agents such as acetazolamide and furosemide, after diagnosis of increased intracranial pressure, resulted in better control of symptoms (Mathew, N. T. et al. Neurology 46:(5), 1226–1230, May 1996). The authors note that these results suggest a link between migraine and idiopathic intracranial hypertension that needs further research.

Drug therapy is tailored to the severity and frequency of migraine headaches. For occasional attacks, abortive treatment may be indicated, but for attacks occurring two or more times per month, or when attacks greatly impact the patient's daily life, prophylactic therapy may be indicated. Serotonin receptor agonists, such as sumatriptan, have been prescribed for abortive therapy. Serotonin receptor agonists are thought to constrict dilated arteries of the brain and thereby alleviate the associated pain. Side effects associated with this therapy include tingling, dizziness, warm-hot sensation, land injection-site reactions. Intravenous administration is contraindicated as a consequence of the potential for coronary vasopasms. Ergotamine-based drugs are classified as vasoconstrictors that specifically counteract the dilation of some arteries and arterioles, primarily the branches of the external carotid artery. To prevent ergotamine rebound phenomena, ergotamine should not be repeated on the second or third day of a migraine attack. Yet, if the drug is stopped abruptly, the patient will experience a severe rebound headache. Excessive consumption of ergotamines may cause symptoms of vasoconstriction, such as cold clammy extremities, and may lead to ergotism.

Drugs used for prophylactic indications include andrenergic beta-blockers such as propranolol, calcium channel blockers, or low-dose anti-epileptics. In particular, anti-epileptic drugs that increase brain levels of GABA, either by increasing GABA synthesis or reducing its breakdown, appear to be effective in preventing migraine in certain individuals. In some patients, tricyclic analgesics, such as amitriptline, can be effective. NMDA receptor antagonist, acting at one of the glutamate receptor subtypes in the brain, inhibits CSD. Drugs or substances currently believed to function as weak NMDA receptor antagonists include dextromethoraphan, magnesium and ketamine. Intravenous magnesium has been successfully used to abort migraine attacks.

Neurotoxicity

A variety of chemical and biological agents, as well as some infectious agents, have neurotoxic effects. A common example is the pathophysiological effect of acute ethanol ingestion. Episodic ethanol intoxications and withdrawals characteristic of binge alcoholism result in brain damage. Animal models designed to mimic the effects of alcohol in the human have demonstrated that a single dose of ethanol given for 5–10 successive days results in neurodegeneration in the entorhinal cortex, dentate gyrus and olfactory bulbs, accompanied by cerebrocortical edema and electrolyte ($Na^+$ and, $K^+$) accumulation. As with other neurodegenerative conditions, research has focused primarily on synaptically based excitotoxic events involving excessive glutamatergic activity, increased intracellular calcium and decreased γ-aminobutyric acid. Co-treatment of brain damage induced by episodic alcohol exposure with an NMDA receptor antagonist, Non-NMDA receptor and $Ca^{2+}$ channel antagonists with furosemide reduces alcohol-dependent cerebrocortical damage by 75–85%, while preventing brain hydration and electrolyte elevations (Collins, M., et al, *FASEB*, vol.12 February 1998). The authors observed that the results suggest that furosemide and related agents might be useful as neuroprotective agents in alcohol abuse.

Cognition, Learning and Memory

The cognitive abilities of mammals are thought to be dependent on cortical processing. It has generally been accepted that the most relevant parameters for describing and understanding cortical function are the spatio-temporal patterns of activity. In particular, long-term potentiation and long-term depression have been implicated in memory and learning and may play a role in cognition. Oscillatory and synchronized activities in the brains of mammals have been correlated with distinct behavioral states.

Synchronization of spontaneous neuronal firing activity is thought to be an important feature of a number of normal and pathophysiological processes in the central nervous system. Examples include synchronized oscillations of population activity such as gamma rhythms in the neocortex, which are thought to be involved in cognition (Singer and Gray, 1995), and theta rhythm in hippocampus, which is thought to play roles in spatial memory and in the induction of synaptic plasticity (Heurta and Lisman 1995; Heurta and Lisman 1996; O'keefe 1993). To date, most research on the processes underlying the generation and maintenance of spontaneous synchronized activity has focused on synaptic mechanisms. However, there is evidence that nonsynaptic mechanisms may also play important roles in the modulation of synchronization in normal and pathological activities in the central nervous system.

Screening of Candidate Compounds and Evaluating Treatment Efficacy

Drug development programs rely on in vitro screening assays and subsequent testing in appropriate animal models to evaluate drug candidates prior to conducting clinical trials using human subjects. Screening methods currently used are generally difficult to scale up to provide the high throughput screening necessary to test the numerous candidate compounds generated by traditional and computational means. Moreover, studies involving cell culture systems and animal model responses frequently don't accurately predict the responses and side effects observed during human clinical trials.

Conventional methods for assessing the effects of various agents or physiological activities on biological materials, in both in vitro and in vivo systems, generally are not highly sensitive or informative. For example, assessment of the effect of a physiological agent, such as a drug, on a population of cells or tissue grown in culture, conventionally provides information relating to the effect of the agent on the cell or tissue population only at specific points in time. Additionally, current assessment techniques generally provide information relating to a single or a small number of parameters. Candidate agents are systematically tested for cytotoxicity, which may be determined as a function of concentration. A population of cells is treated and, at one or several time points following treatment, cell survival is measured. Cytotoxicity assays generally do not provide any information relating to the cause(s) or time course of cell death.

Similarly, agents are frequently evaluated based on their physiological effects, for example, on a particular metabolic function or metabolite. An agent is administered to a population of cells or a tissue sample, and the metabolic function or metabolite of interest is assayed to assess the effect of the agent. This type of assay provides useful information, but it does not provide information relating to the mechanism of action, the effect on other metabolites or metabolic functions, the time course of the physiological effect, general cell or tissue health, or the like.

U.S. Pat. Nos. 5,902,732 and 5,976,825 disclose methods for screening drug candidate compounds for anti-epileptic activity using glial cells in culture by osoniotically shocking glial cells, introducing a drug candidate, and assessing whether the drug candidate is capable of abating changes in glial cell swelling. This patent also discloses a method for screening drug candidate compounds for activity to prevent or treat symptoms of Alzheimer's disease, or to prevent CNS damage resulting from ischemia, by adding a sensitization agent capable of inducing apoptosis and an osmotic stressing agent to CNS cells, adding the drug candidate, and assessing whether the drug candidate is capable of abating cell swelling. A method for determining the viability and health of living cells inside polymeric tissue implants is also disclosed, involving measuring dimensions of living cells inside the polymeric matrix, osmotically shocking the cells, and then assessing changes in cell swelling. Assessment of cell swelling activity is achieved by measuring intrinsic optical signals using an optical detection system.

SUMMARY OF THE INVENTION

Selected treatment compositions and methods of the present invention are useful for treating central nervous system conditions, including seizures and seizure disorders, epilepsy, including status epilepticus, migraine headaches, cortical spreading depression, intracranial hypertension, neuropsychiatric disorders, and central nervous system edema. Selected treatment compositions and methods of the present invention are also suitable for treating or protecting from the pathophysiological effects of neurotoxic agents such as ethanol and certain infectious agents, and for treating the pathophysiological effects of head trauma, stroke, ischemia and hypoxia. According to another embodiment, treatment agents and methods of the present invention improve function in certain cortical tissue, such as in cortical centers of cognition, learning and memory. Additionally, treatment agents and methods of the present invention are useful for treating pain by affecting or modulating the conduction of impulses associated with pain in the peripheral nervous system. Treatment compositions and methods of the present invention may be used episodically or prophylactically and are suitable for both human and veterinary applications.

Methods and compositions of the present invention involve treatment of various conditions of the central and peripheral nervous systems by means of non-synaptic mechanisms and, more specifically, by modulating the synchronization of neuronal population activity. According to a preferred embodiment, the synchronization of neuronal population activity is manipulated by modulating anionic concentrations and gradients in the central and/or peripheral nervous systems. Ion dependent cotransporter antagonists are suitable treatment compositions, anion cotransporter antagonists are preferred treatment compositions, and cation-chloride cotransporter antagonists are especially preferred treatment compositions. According to one embodiment, $Na^+,K^+,2Cl^-$ chloride cotransporter antagonists are especially preferred treatment agents for modulating the synchronization of neuronal population activity. Anion cotransporter antagonists are useful for treating conditions such as seizures, epilepsy and status epilepticus, cortical spreading depression and migraine headaches, intracranial hypertension, neuropsychiatric disorders, central nervous system edema, for treating or protecting from the pathophysiological effects of neurotoxic agents such as ethanol and certain infectious agents, and for reducing the perception of pain. Chloride cotransporter agonists are preferred treatment agents, and cation-chloride cotransporter agonists are especially preferred treatment agents for improving function in cortical areas associated with cognition, learning and memory, for example. Methods for screening candidate compounds for ion-dependent cotransporter agonist and antagonist activity, and for efficacy in treating various conditions and disorders are also provided.

Reference to the methods and compositions of the present invention using "non-synaptic" mechanisms means that mechanisms associated with neuronal excitability, such as the release or activity of transmitters, or the release or activity of inhibitors, are not affected by methods and agents of the present invention. Similarly, ion channels and receptors are not directly affected by methods and compositions of the present invention. Rather, the methods and treatment agents of the present invention affect the synchronization, or relative synchrony, neuronal population activity. Preferred methods and treatment agents of the present invention modulate the extracellular anionic chloride concentration and/or the ion gradients in the central or peripheral nervous system without substantially affecting neuronal excitability.

One aspect of the present invention relates to treatment agents and methods for modulating the synchronization of neuronal discharges by diminishing or eliminating hypersynchronization of neuronal population activity associated with seizures and other pathophysiologies of the central nervous system. In one embodiment, the treatment composition is capable of modulating the anion concentration, preferably the chloride concentration, in the extracellular space in the central nervous system. In a preferred embodiment, the treatment agent is a chloride cotransporter antagonist, and in another preferred embodiment, the treatment agent is a cation chloride cotransporter antagonist, and in an especially preferred embodiment, the treatment composition is a glial cell $Na^+,K^+,2Cl^-$ cotransporter antagonist. According to yet another preferred embodiment, the treatment agent has a high level of cation-chloride cotransporter antagonist activity, in glial cells, and has a lower level of ion-dependent cotransporter activity in neuronal and kidney cells. Preferred agents for treatment of central nervous system conditions are preferably capable of crossing the blood brain barrier, or are administered using delivery systems that facilitate delivery of agents to the central nervous system.

In general, loop diuretics, such as furosemide, bumetanide, ethacrynic acid, and the like, exhibit ion-dependent cotransporter antagonist activity and are suitable for use as treatment compositions of the present invention. Although such loop diuretics produce the desired modulation of the extracellular anionic chloride concentrations and ionic gradients and, hence, modulation of synchronization of neuronal population activity, they may also produce other, undesired effects. Furosemide, for example, acts as a cation-chloride cotransporter antagonist in both glial and neuronal cells, as well as in the kidney. Especially preferred treatment agents of the present invention, exhibiting ion-dependent cotransporter antagonist activity, exhibit a high degree of activity in glial cell populations, and exhibit a lesser degree of activity in neuronal and renal cell populations.

Methods for treating status epilepticus involve administering an ion-dependent cotransporter antagonist, preferably a cation-chloride cotransporter antagonist, in combination with another treatment agent. Furosemide and other loop diuretics are suitable cation-chloride cotransporter antagonists. Experimental studies have shown that furosemide treatment produces a transient and early increase in synchronization of neuronal population activity, followed by a persistent and complete disruption of the hypersynchronization characteristic of epileptiform activity. Treatment of status epilepticus, according to the present invention, involves administration of an ion-dependent cotransporter antagonist, preferably a cation-chloride cotransporter antagonists, such as furosemide, in combination with another agent, such as a barbiturate, that is capable of treating the symptoms associated with the transient and early increase in synchronization of neuronal population activity observed upon administration of furosemide.

Methods and treatment compositions for treating seizures and seizure disorders, epilepsy, migraine headaches, cortical spreading depression intracranial hypertension, neuropsychiatric disorders, and for treating or protecting from the pathophysiological effects of neurotoxic agents, head trauma, stroke, ischemia and hypoxia involve modulating the synchronization of neuronal population activity, preferably by modulating ion gradients in the central nervous system. Ion-dependent cotransporter antagonists are preferred treatment compositions, and cation-chloride cotransporter antagonists are especially preferred treatment compositions. If the ion-dependent cotransporter antagonist treatment composition has activity, for example, with respect to glial cells, but has lower or substantially no activity with respect to neuronal cells, it is suitable for administration alone. If the ion-dependent cotransporter antagonist treatment composition has activity with respect to neuronal as well as other types of cells, it is preferably administered in combination with another agent, such as conventional anti-epleptic or anti-convulsant agent.

Another aspect of the present invention relates to methods and agents for relieving pain, or the perception of pain, by effecting or modulating propagation of action potentials or conduction of impulses in certain nerve fibers in the peripheral nervous system. More specifically, changes in extracellular ionic concentrations and ionic gradients in cells in the peripheral nervous system, affected by ion-dependent cotransporters, diminishes the perception or sensation of pain. Ion-dependent cotransporter antagonists and, preferably, cation-chloride cotransporter antagonists, delivered to the peripheral nervous system, are preferred treatment compositions for the reduction of pain.

Yet another aspect of the present invention relates to methods and agents for enhancing the function of cognitive, learning and memory centers in the central nervous system. Enhanced synchronization of neuronal population activity improves function in centers associated with cognitive abilities, learning and memory in central nervous system cortex. Treatment compositions and methods of the present invention for enhancing cognitive, learning and memory functions involve modulating the synchronization and timing of neuronal population activity, preferably by enhancing synchronization and coordinating timing. According to one embodiment, enhancement of synchronization is achieved by administering an agent capable of modulating extracellular anionic chloride concentrations and ionic gradients in the brain. Ion-dependent cotransporter agonists are preferred treatment agents, and cation-chloride cotransporter agonists are especially preferred. Methods for screening candidate compounds for ion-dependent cotransporter agonist activity are also provided.

Screening methods and systems of the present invention employ optical, or spectroscopic, detection techniques to assess the physiological state of biological materials including cells, tissues, organs, subcellular components and intact organisms. The biological materials may be of human, animal, or plant origin, or they may be derived from any such materials. Static and dynamic changes in the geometrical structure and/or intrinsic optical properties of the biological materials in response to the administration of a physiological challenge or a test agent, are indicative and predictive of changes in the physiological state or health of the biological material.

Two different classes of dynamic phenomena are observed in viable biological materials using optical detection techniques: (1) geometrical changes in the diameter, volume, conformation, intracellular space of individual cells or extracellular space surrounding individual cells; and (2) changes in one or more intrinsic optical properties of individual cells or of cell populations, such as light scattering, reflection, absorption, refraction, diffraction, birefringence, refractive index, Kerr effect, and the like. Both classes of phenomena may be observed statically or dynamically, with or without the aid of a contrast enhancing agent. Geometrical changes may be assessed directly by measuring (or approximating) the geometrical properties of individual cells, or indirectly by observing changes in the optical properties of cells. Changes in optical properties of individual cells or cell populations may be assessed directly using systems of the present invention.

Observation and interpretation of geometrical and/or intrinsic optical properties of individual cells or cell populations is achieved in both in vitro and in vivo systems without altering characteristics of the sample by applying physiologically invasive materials, such as fixatives. Physiologically non-invasive contrast enhancing agents, such as vital dyes, may be used in desired applications to enhance the sensitivity of optical detection techniques. In applications employing contrast enhancing agents, the optical detection techniques are used to assess extrinsic optical properties of the biological materials.

Detection and analysis of the geometrical and/or intrinsic optical properties of individual cells or sample cell populations provides information permitting classification of the physiological state of individual cells or sample cell populations. Based on analysis of the geometrical and/or optical properties of a sample cell population, the sample may be classified as viable or non-viable, apoptotic, necrotic, proliferating, in a state of activity, inhibition, synchronization, or the like, or in any of a variety of physiological states, all of which produce distinct geometrical and/or optical profiles. The methods and systems of the present invention therefore provide for identification of the physiological state of a sample population and differentiation among various physiological states.

An important application of the methods and systems of the present invention involves screening cell populations to assess the effect(s) of exposure to various types of test agents and test conditions. The effect of various test agents and conditions may be evaluated on both normal and pathological sample populations. Safety and cytoxicity testing is conducted by exposing a sample population to a test agent or test condition and assessing the physiological state of the sample population using optical techniques at one or more time points following administration of the test agent or test condition. Such testing may be conducted on various sample populations to determine how a test agent or condition affects a desired target sample population, as well as to predict whether a test agent or condition produces physiological side effects on sample populations that are not the target of the test agent or condition.

According to a preferred embodiment, a pathological condition is simulated in biological materials prior to administration of a test agent or test condition to assess the suitability of the test agent or condition for treating the disease state or compromised condition. Exposure of sample populations to a physiological challenge, such as a change in extracellular osmolarity or ion concentration, altered oxygen or nutrient or metabolite conditions, drugs or diagnostic or therapeutic agents, a disturbance in ion homeostasis, electrical stimulation, inflammation, infection with various agents, radiation, and the like, may simulate a pathological state at a cellular or tissue level. Subsequent exposure of the sample populations a test agent or condition and detection and analysis of changes in geometrical and/or optical properties of the sample populations provides information relating to the physiological state of the sample populations produced by the test agent or condition. Screening techniques may be adapted for use with various types of cell sample populations maintained in vitro under appropriate cell culture conditions to provide a high throughput, automated screening system. Alternatively, screening techniques may be adapted to examine cell and tissue populations using various animal models to assess the effect of a physiological challenge and/or administration of a test agent on various cell populations in animal models in situ. Moreover, because the screening techniques of the present invention are physiologically non-invasive and use spectroscopic techniques, they may be adapted to examine cell and tissue populations in humans, in situ, to assess or monitor a patient's condition, and to assess or monitor the efficacy of a treatment agent or regimen.

Changes in geometrical and/or optical properties of individual cells or cell populations may be determined by reference to empirically determined standards for specific cell types, cell densities and various physiological states, or appropriate controls may be run in tandem with the test samples to provide direct comparative data. Data is collected and, preferably, stored at multiple time points to provide data relating to the time course of the effect of a test agent or condition on sample populations. Strategies for designing screening protocols, including appropriate controls, multiple samples for screening various dosages, activities, and the like, are well known in the art and may be adapted for use with the methods and systems of the present invention.

BRIEF DESCRIPTION OF THE DRAWINGS

FIGS. 1A, 1A1, 1B, 1B1, 1C, 1C1 and 1D show the effect of furosemide on stimulation evoked after discharge activity in rat hippocampal slices.

FIGS. 3A–3H show furosemide blockade of kainic acid-evoked electrical "status epilepticus" in urethane-anesthetized rats, with EKG recordings shown in the upper traces and cortical EEG recordings shown in the bottom traces.

FIGS. 4A and 4B show a schematic diagram of ion cotransport under conditions of reduced chloride concentration.

DETAILED DESCRIPTION OF THE INVENTION

Figure 2A:
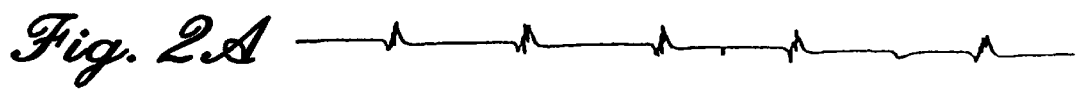
FIGS. 2A–2R show furosemide blockade of spontaneous epileptiform burst discharges across a spectrum of in vitro models.

Preferred treatment agents and methods of the present invention, for use in treating seizures and other pathophysiological disorders of the central nervous system, modulate or disrupt the synchrony of neuronal population activity in areas of heightened synchronization, such as epileptic foci.

As described in detail below and illustrated in the examples, movement of ions and modulation of ionic gradients by means of ion-dependent cotransporters, preferably cation-chloride dependent cotranporters, is critical to regulation of neuronal synchronization. Chloride cotransport function has long been thought to be directed primarily to movement of chloride out of cells. The sodium independent transporter, which has been shown to be neuronally localized, moves chloride ions out of neurons. Blockade of this transporter, such as by administration of the loop diuretic furosemide, leads to hyperexcitability, which is the short-term response to cation-chloride cotransporters such as furosemide. However, the long-term response to furosemide demonstrates that the inward, sodium-dependent movement of chloride ions, mediated by the glial associated $Na^+,K^+,2Cl^-$ cotransporter, plays an active role in blocking neuronal synchronization and, hence, seizure, without affecting excitability and stimulus-evoked cellular activity.

According to one embodiment, compositions and methods of the present invention for treating seizures and certain cortical conditions, such as seizures, seizure disorders, epilepsy, including status epilepticus, migraine headaches, cortical spreading depression, intracranial hypertension, neuropsychiatric disorders, central nervous system edema, neural toxicity, such as toxicity induced by alcohol exposure, pathophysiological effects of head trauma, stroke, ischemia and hypoxia, and other conditions resulting from or producing ionic imbalances in the central nervous system, or synchronized discharges of neuronal populations, modulate ion-dependent cotransporter activity. Treatment agents of the present invention for treating seizure disorders and other cortical conditions comprise ion-dependent cotransporter antagonists, preferably cation-chloride cotransporter antagonists. According to a preferred embodiment, agents and methods of the present invention preferentially act on the $Na^+,K^+,2Cl^-$ chloride-dependent cotransport systems of glial cells, and have reduced activity on the chloride-dependent cotransport systems of other cell types, such as neurons and renal cells.

In another embodiment, materials and methods of the present invention are used to treat migraine headache and its precursor condition, cortical spreading depression (CSD). During spreading depression, profound ionic perturbations occur, which include interstitial acidification, extracellular potassium accumulation and redistribution of sodium and chloride ions to intracellular compartments. In addition, prolonged glial swelling occurs as a homeostatic response to altered ionic extracellular fluid composition and interstitial neurotransmitter and fatty acid accumulation. Materials and methods of the present invention inhibit the generation and duration of CSD by blocking the inward sodium-dependent movement of chloride ions mediated by the chloride-dependent cotransporters. Treatment compositions of the present invention for treating migraine headaches and cortical spreading depression comprise cation-chloride cotransporter antagonists. According to a preferred embodiment, agents and methods of the present invention for treating migraine headaches and cortical spreading depression preferentially act on the $Na^+,K^+,2Cl^-$ chloride-dependent cotransport system of glial cells and have reduced activity on the chloride-dependent cotransport systems of other cell types, particularly neurons and renal cells.

Yet another aspect of the present invention involves treatment of neurotoxicity attributable to a variety of chemical and biological agents, as well as some infectious agents. Compositions and methods of the present invention are especially effective in reducing the neurodegenerative effects of acute ethanol ingestion. Additionally, compositions of the present invention may be administered prophylactically to protect cortical tissue from the effects of neurotoxicity attributable, for example, to acute ethanol ingestion. Treatment compositions of the present invention for treating, or for prophylactic administration to protect from neurotoxicity, comprise ion-dependent cotransporter antagonists, preferably cation-chloride cotransporter antagonists. According to a preferred embodiment, agents and methods of the present invention for treating migraine headaches and cortical spreading depression preferentially act on the $Na^+,K^+,2Cl^-$ chloride-dependent cotransport system of glial cells and have reduced activity on the chloride-dependent cotransport systems of other cells types, such as neurons and renal cells.

According to yet another embodiment, compositions and methods of the present invention may be used to alleviate the perception or sensation of pain. In this embodiment, compositions and methods of the present invention affect or modulate the propagation of action potentials in unmyelinated fibers in the peripheral nervous system and, thus, diminish the perception or sensation of pain. Agents of the present invention for treating, or for prophylactic administration to protect from pain, ion-dependent chloride cotransporter antagonists, preferably cation-chloride transporter antagonists, that modulate the extracellular ionic concentration and/or the ionic gradients in the peripheral nervous system. According to a preferred embodiment, compositions of the present invention for treating pain preferentially act on the cation-chloride cotransport system of glial cells, or Schwantz cells, and have reduced activity on the chloride-dependent cotransport systems of other types of cells, such as neurons and renal cells.

In yet another embodiment, materials and methods of the present invention may be used to enhance certain cortical functions, such as cognition, learning and memory. For this application, compositions and methods of the present invention modulate and enhance, rather than disrupt, the synchronization of neuronal population activity. Compositions of the present invention for enhancing cortical function, such as cognition, learning and memory, comprise ion-dependent cotransport agonists preferably cation-chloride cotransport agonists.

Compositions of the subject invention are suitable for human and veterinary applications and are preferably delivered as pharmaceutical compositions. Pharmaceutical compositions comprise one or more treatment agents and a physiologically acceptable carrier. Pharmaceutical compositions of the present invention may also contain other compounds, which may be biologically active or inactive. For example, one or more compounds from the class of chloride cotransporter agonists or antagonists may be combined with another agent, in a treatment combination, and administered according to a treatment regimen of the present invention. Such combinations may be administered as separate compositions, or may be combined for delivery in a complementary delivery system, or may be formulated in a combined composition, such as a mixture or a fusion compound.

While any suitable carrier known to those of ordinary skill in the art may be employed in the pharmaceutical compositions of this invention, the preferred carrier depends upon the preferred mode of administration. Compositions of the present invention may be formulated for any appropriate mode of administration, including for example, topical, oral, nasal, rectal, intravenous, intracranial, spinal tap, intraperitoneal, transdermal, subcutaneous or intramuscular administration. For parenteral administration, such as by subcutaneous injection, the carrier preferably comprises water, saline, glycerin, propylene glycol, alcohol, a fat, a wax and/or a buffer. For oral administration, any of the above carriers, or a solid carrier such as mannitol, lactose, starch, magnesium stearate, sodium lauryl sulphate, lactose, sodium citrate, calcium carbonate, calcium phosphate, silicates, polyethylene glycol, sodium saccharine, talcum, cellulose, glucose, sucrose, dyes, and magnesium carbonate, may be employed. For rectal administration, an aqueous gel formulation, or other suitable formulations that are well known in the art may be administered. Solid, compositions may also be employed as fillers in soft and hard filled gelatin capsules. Preferred materials for this include lactose or mild sugar and high molecular weight polyethylene glycols. When aqueous suspensions or elixirs are desired for oral administration, the essential active ingredient therein may be combined with various sweetening, or flavoring agents, coloring matter or dyes and, if desired, emulsifying or suspending agents, together with diluents such as water, ethanol, propylene glycol, glycerin and combinations thereof.

Local intracerebral administration, which reduces systemic distribution of the treatment composition(s), may be provided by perfusion via a mechanized delivery system, such as an osmotic pump, or by implantation of a dosage of the treatment composition(s) incorporated in a non-reactive carrier to provide controlled diffusion of the treatment composition over a time course to a circumscribed region of the brain. Other types of time release formulations may also be implemented. Additionally, direct administration into the cerebral spinal fluid via the spinal cord by injection, osmotic pump or other means is preferred for certain applications.

The compositions described herein may be administered as part of a sustained release formulation. Such formulations may generally be prepared using well known technology and administered by, for example, oral, rectal or transdermal, delivery systems, or by implantation of a formulation or therapeutic device at one or more desired target site(s). Sustained-release formulations may contain a treatment composition comprising an ion-dependent cotransporter agonist or antagonist alone, or in combination with a second treatment agent, dispersed in a carrier matrix and/or contained within a reservoir surrounded by a rate controlling membrane. Carriers for use within such formulations are biocompatible, and may also be biodegradable. According to one embodiment, the sustained release formulation provides a relatively constant level of active composition release. According to another embodiment, the sustained release formulation is contained in a device that may be actuated by the subject or medical personnel, upon onset of certain symptoms, for example, to deliver predetermined dosages of the treatment composition. The amount of the treatment composition contained within a sustained release formulation depends upon the site of implantation, the rate and expected duration of release, and the nature of the condition to be treated or prevented.

Compositions of the present invention for treatment of cortical disorders or conditions, such as seizures, seizure disorders, epilepsy, status epilepticus, migraine, spreading depression, and other conditions characterized by synchronized neuronal population activity, as well as intracranial hypertension, central nervous system edema, neurotoxicity, and the like, are preferably administered using a formulation and a route of administration that facilitates delivery of the treatment composition(s) to the central nervous system. Treatment compositions, such as ion-dependent cotransporter antagonists, preferably cation-chloride cotransporter antagonists, may be formulated to facilitate crossing of the blood brain barrier, or may be co-administered with an agent that crosses the blood brain barrier. Treatment compositions may be delivered in liposome formulations, for example, that cross the blood brain barrier, or may be co-administered with other compounds, such as bradykinins, bradykinin analogs or derivatives, or other compounds that cross the blood brain barrier. Alternatively, treatment compositions of the present invention may be delivered using a spinal tap that places the treatment composition directly in the circulating cerebrospinal fluid. For some treatment conditions, such as chronic epilepsy, episodic seizures, and during some episodes of spreading depression and migraine headache, there may be transient Or permanent breakdowns of the blood brain barrier and specialized formulation of the treatment composition to cross the blood brain barrier is not necessary.

Routes and frequency of administration of the therapeutic compositions disclosed herein, as well as dosages, vary according to the indication, and from individual to individual, and may be readily established using standard techniques. In general, appropriate dosages and treatment regimen provide the active composition(s) in an amount sufficient to provide therapeutic and/or prophylactic benefit. Dosages and treatment regimen may be established by monitoring improved clinical outcomes in treated patients as compared to non-treated patients. A suitable dose is an amount of a compound that, when administered as described above, produces a therapeutic response in a patient. Therapeutically effective dosages and treatment regimen will depend on the condition, the severity of the condition, and the general state of the patient being treated. Since the pharmacokinetics and pharmacodynamics of the treatment compositions of the present invention vary in different patients, a preferred method for determining a therapeutically effective dosage in a patient is to gradually escalate the dosage and monitor the clinical and laboratory indicia. Appropriate dosages and treatment regimen for treatment of acute episodic conditions, chronic conditions, or prophylaxis will necessarily vary to accommodate the condition of the patient.

In a representative therapeutic treatment regimen, a pharmaceutical preparation of the present invention is administered alone or, optionally, in combination with a second agent. In combination treatment for seizures and seizure-related disorders, such as epilepsy, treatment compositions of the present invention comprising an ion-dependent cotransporter antagonist, preferably a cation-chloride cotransporter antagonist, is administered in combination with one or more anti-convulsant or antiepileptic drugs using a delivery system that delivers the treatment composition(s) to the central nervous system. Often the dose of the second agent may be less than the standard dosage as a consequence of the neurophysiological activity of the ion-dependent cotransporter antagonist. Illustrative second agents for treatment in combination with the subject compositions comprising ion-dependent antagonists, include, for example, phenytoin, carbamazepine, barbiturates, phenobarbital, phenobarbital, mephobarbital, trimethadione, mephenytoin, paramethadione, phenthenylate, phenacemide, metharbital, benzchlorpropamide, phensuximide, priraidone, methsuximide, ethotoin, aminoglutethinide, diazepam, clonazepam, clorazepate, fosphenytoin, ethosuximide, valproate, felbamate, gabapentin, lamotrigine, topiramate, vigrabatrin, tiagabine, ziamide, clobazam, thiopental, midazolam, propofol, levetiracetam, oxcarbazepine, CCPene, and GYK152466.

As can be readily appreciated, the above-noted compounds are only examples of suitable treatment combinations, and other compounds or similar classes of compounds are also suitable.

In one preferred embodiment for treating status epilepticus, a treatment composition of the present invention having ion-dependent cotransporter antagonist activity, preferably cation-chloride cotransporter activity, such as furosemide or another loop diuretic, is administered in combination with a traditional anti-seizure agent, such as a barbiturate. In this treatment regimen, the barbiturate, or another anti-seizure agent acts, via synaptic mechanisms, to damp the hyperexcitability of the neuronal population activity and to treat the symptoms of the seizure. The ion-dependent cotransporter antagonist acts, via non-synaptic mechanisms, to damp the hypersynchronization of neuronal population activity in the area of the seizure activity. This combination of treatment compositions may be administered on an emergency basis for treatment of status epilepticus and may be administered using a variety of delivery techniques that deliver the treatment compositions to the central nervous system. The present invention thus contemplates treatment regimen involving administration of a combination of one or more ion-dependent cotransporter antagonist(s), preferably one or more cation-chloride transporter antagonist, with one or more traditional anti-seizure agent(s) selected, for example, from one of the following: phenytoin, carbamazepine, barbiturates, Phenobarbital, pentobarbital, mephobarbital, trimethadione, mephenytoin, paramethadione, phenthenylate, phenacemide, metharbital, benzchlorpropamide, phensuximide, primidone, methsuximide, ethotoin, aminoglutethimide, diazepam, clonazeparn, clorazepate, fosphenytoin, ethosuxirmide, valproate, felbamate, gabapentin, lamotrigine, topiramate, vigrabatrin, tiagabine, zonisamide, clobazam, thiopental, midazolam, propofol, levetiracetam, oxcarbazepine, CCPene, and GYK152466. The present invention also contemplates a combination comprising one or more chloride cotransporter antagonists with one or more anti-convulsant or anti-seizure agents. According to one embodiment, the combination comprises a preselected dosage of one or more anti-convulsant or anti-seizure agents sufficient to reduce hyperexcitability for a period of two hours or less, with a preselected dosage of one or more anion-dependent cotransporter antagonists sufficient to reduce hypersynchronization of neuronal population activity for a period of two hours or more.

According to a preferred embodiment, the present invention contemplates a container having a combination of preselected dosages of furosemide, or another ion-dependent cotransporter antagonist, with a barbiturate. The term "container" contemplates packets, jars, vials, bottles and other containers for treatment compositions in a solid or particulate delivery system, as well as syringes and other liquid containment means, such as various types of bags, vials, bottles, and the like, having contained therein, preselected dosages of the combination agents of the present invention. The combination may be packaged and administered such that each composition of the combination is packaged and administered separately, or, the compositions may be packaged and administered as a mixture for simultaneous administration. The present invention also contemplates an emergency or surgical suite in a hospital, clinic, mobile unit, or the like, equipped with one or more containers having a combination of preselected dosages of an ion-dependent cotransporter antagonist with an anti-convulsant or anti-epileptic agent.

Treatment compositions of the present invention for treating migraine headaches and cortical spreading depression comprise an ion-dependent cotransporter antagonist, preferably a cation-chloride cotransporter antagonist, optionally in combination with one or more other therapeutic compositions. The ion-dependent cotransporter antagonist may be administered either together or in conjunction with other treatment modalities, or separately, for example at different times or using different delivery techniques. Often the dose of a conventional treatment composition for migraine or spreading depression may be reduced to less than a standard dosage when the treatment is combined with administration of an ion-dependent cotransporter antagonist. The present invention thus contemplates treatment regimen involving administration of a combination of one or more ion-dependent cotransporter antagonist(s) with one or more traditional migraine headache or spreading depression agent (s) selected, for example, from one of the following: serotonin receptor agonists, ergotamine, dihydroergotamine, sumatriptan, propranolol, metoprolol, atenolol, timolol, nadolol, nifeddipine, nimodipine, verapamil, aspirin, ketoprofen, tofenamic acid, mefenamic acid, naproxen, methysergide, paracetamol, clonidine, lisuride, iprazochrome, butalbital, benzodiazepines and divalproex sodium. As can be readily appreciated, the above-noted compounds are only examples of suitable combined treatments and other compounds or similar classes of compounds are equally suitable.

Treatment compositions of the present invention for treating intracranial hypertension, neuropsychiatric disorders, central nervous system edema, and for treating or protecting from neurotoxicity resulting from exposure to neurotoxic agents such as ethanol, infectious agents, and the like, comprise an ion-dependent cotransporter antagonist. The treatment composition may optionally be administered in combination with one or more other therapeutic compositions. Delivery systems providing delivery of the ion-dependent cotransporter antagonist composition to the central nervous system are preferred.

Treatment compositions of the present invention for reducing pain comprise an ion-dependent cotransporter antagonist, preferably a cation-chloride cotransporter antagonist, optionally in combination with one or more other therapeutic compositions. Such treatment compositions preferably do not have the ability to cross the blood brain barrier and circulate in the peripheral nervous system only. Delivery systems providing delivery of the ion-dependent cotransporter antagonist composition to the peripheral nervous system are preferred.

Treatment compositions of the present invention for enhancing cortical function in regions such as cognitive, learning and memory centers comprise an ion-dependent cotransporter agonists, preferably a cation-chloride cotransporter agonist, optionally in combination with one or more other therapeutic compositions. Suitable delivery systems provide delivery of the ion-dependent cotransporter agonist treatment composition preferentially to the central nervous system, and more preferably to localized cortical centers of cognition, learning and/or memory.

Methods and systems of the present invention may also be used to evaluate candidate compounds and treatment regimen for diagnosis and treatment of various disorders and conditions. Various techniques for generating candidate compounds potentially having the desired ion-dependent cotransporter agonist or antagonist activity may be employed. Candidate compounds may be generated using well known combinatorial chemistry or molecular modeling techniques starting with known ion-dependent cotransporter antagonists, such as loop diuretics, including furosemide, bumetanide, ethacrinic acid, and the like, and related compounds, and modifying those compounds in ways that would be expected to confer the desired activities and specificities. Similarly, candidate chloride cotransporter agonist compounds may be generated using combinatorial chemistry techniques or molecular modeling techniques starting with known ion-dependent cotransporter agonists, and related compounds, and modifying those compounds in ways that would be expected to confer the desired activities and specificities. Methods for screening candidate compounds for desired activities are described below.

According to one embodiment, methods and systems of the present invention acquire and compare data representative of one or more dimensional properties of individual cells or cell samples. Techniques for acquisition, processing and analysis of data relating to optical properties are known and are described, for example, in U.S. Pat. Nos. 5,43,8989, 5,465,718, 5,845,639, 5,699,798, 5,902,732 and 5,976,825, each of which is incorporated by reference herein in its entirety. Acquisition of data relating to dimensional properties of individual cells is described below. Acquisition and analysis of data relating to dimensional properties may be achieved using the same or similar methods and apparatus described with reference to optical properties.

In sparsely populated cell samples, cell areas may be approximated using a single plane of focus. If it is desired to calculate volume, the z-axis (focus) can be automatically adjusted as well. For example, as an automated and controlled stage moves, an optically transparent container containing the sample population is positioned so that a series of data sets for multiple, spatially resolved areas of interest can be acquired, each image being acquired at a predetermined focal plane. The volume for each z-plane can be approximated (see algorithm below) and then the volumes for each z-coordinate added together.

General techniques for approximating cell areas and volumes, based on Doughty, S., "Calculating property for solids of revolution," *Machine Design*, pp 184–186, Dec. 10, 1981, are described below. These techniques are based on Green's theorem:

$$\int (Pdx + Qdy) \quad \int\int\left(\frac{\partial Q}{\partial x} - \frac{\partial P}{\partial y}\right)dxdy$$

(boundary) (area)

Individual cells are examined using an appropriate magnifying device. Edge detection of cell boundaries is achieved using, for example, a Sobel operator. The boundary is approximated by fitting it to a plurality of straight line segments of "n", line segments by "n" nodes. The integration of the boundary may be taken as "n" line integrals as follows:

$$\int_\Gamma (\ldots)ds = \int_{X_1,Y_1}^{X_2,Y_2} (\ldots)ds + \int_{X_2,Y_2}^{X_3,Y_3} (\ldots)ds + \ldots + \int_{X_n,Y_n}^{X_1,Y_1} (\ldots)ds$$

There are three cases:
Case 1: a vertical line, x=constant;
Case 2: a horizontal line, y=constant;
Case 3: an inclined line, $y=5_i(x-x_i)+y_i$
The area is thus:

$$A = \int\int_A 1 \cdot dxdy$$

To apply Green's theorem, the integral can be considered in the, form of $\delta Q/\delta x - \delta P/\delta y$ and appropriate functions can be devised, e.g., $P(x, y)$ and $Q(x, y)$. For an area calculation, consider $Q(x, y)=0$ so that $\int Qdy=0$, and let $P=-y$ so that $\delta P/\delta y=-1$. Then, the area can be calculated as follows:

$$A = \int\int 1 dxdy = -\int\int \delta P/\delta y \, dxdy$$

$$= \int\int (2Q/\delta x - \delta P/\delta y)dxdy$$

$$= \int (Pdx + Qdy)$$

(Green's Theorem)

$$= \int Pdx$$

$$= -\int ydx$$

Case2: $\Delta A = y_i(x_{i+1}-x_i)$ Case 1=0
Case3: $\Delta A = -[\frac{1}{2}5_i(x^2_{i+1}-x_i^2)+(y_i-5_ix_i)(x_{i+1}-x_i)]A = \Sigma\Delta A$ For volume calculations, conventional edge detection using, for example, a Sobel operator, can be used to focus through an individual cell, which can be divided into a plurality (n) of individual, planar sections. The volume for each of the "n" sections can be calculated as $\Delta V_i = \Delta z_i \cdot \Delta A$; and the volume of the entire cell can be approximated as: $V = \Sigma\Delta V_i$. The determination and comparison of cell areas and volumes is preferably accomplished using computer hardware and/or software implementations.

According to another embodiment, methods and systems of the, present invention acquire and compare data representative of one or more optical properties of individual cells or areas of interest in cell sample populations. Changes in optical properties that are indicative of physiological activity and that may be detected include, for example, reflection, refraction, diffraction, absorption, scattering, birefringence, refractive index, Kerr effect, and the like. Changes in optical properties are detected directly using photosensitive elements and, optionally, optical elements that enhance the detected optical properties.

High resolution detection of dynamic geometrical and optical properties indicative of physiological activity may be accomplished without using dyes or other types of contrast enhancing agents according to the methods and apparatus of the present invention, as evidenced by the U.S. Patents incorporated herein by reference. Many of the assessment techniques and apparatus of the present invention are physiologically noninvasive, in that detection and analysis of geometrical and/or intrinsic optical information does not require direct contact of the area of interest with any agents such as dyes, oils, devices, or the like. For particular applications, it may, however, be useful to administer contrast enhancing agents that amplify differences in an optical property being detected as a function of physiological activity prior to acquiring subsequent data and generating a comparison. The use of contrast enhancing agents is described in detail, with reference to optical imaging of tumor and non-tumor tissue, in U.S. Pat. Nos. 5,465,718 and 5,438,989, which are incorporated by reference herein in their entireties. Suitable contrast enhancing agents include fluorescent and phosphorescent materials, dyes that bind to cell membranes, optical probes that preferentially accumulate in blood or in the intracellular space, phase resonance dye pairs, and the like. Detectors appropriate for use with such contrast enhancing agents are well known in the art.

Numerous devices for acquiring, processing and displaying data representative of one or more geometrical and/or optical properties of a cell sample population in culture or an area of interest in situ in an animal model or human subject may be employed. One preferred device is a camera that acquires images of one or more areas of interest at predetermined time intervals that can be compared to identify areas of changes in geometrical and/or optical properties that indicate physiological activity or dysfunction. The data acquisition device preferably incorporates or is used in conjunction with a device that magnifies the area of interest, such as a microscope. Magnification sufficient to provide resolution of individual cells is preferred. An inverted microscope such as a Nikon Diophot 300 is suitable.

For high throughput screening techniques using cell sample populations maintained under culture conditions, samples in optically transparent containers such as flasks, plates and multi-well plates, may be placed on an automated stage that is controlled and moved in a programmed fashion to permit periodic examination of individual cells or cell populations according to a programmed schedule. For example, a multi-well culture plate having a plurality of cell samples may be placed on an automated and controllable microscope stage. The stage is controlled by an automated microcontroller so that it automatically moves into position over each culture well. A data set relating to geometrical and/or optical properties of individual cells or a cell population is acquired for each position. In this manner, the system can rapidly and systematically acquire data corresponding to many samples. The physiological environment in selected wells may be altered by exposure to a physiological challenge, test agent or test condition, and the system may continue to automatically acquire data from the same wells in each culture plate at predetermined time intervals following treatment, with data acquired from various treatment wells being compared to data acquired from various control wells or empirically determined controls.

Acquisition of data representative of one or more geometrical and/or optical properties preferably provides high spatial resolution as well, so that geometrical or optical data corresponding to a particular spatial location is acquired at various, time intervals for comparison. In this fashion, data acquired from single cells or highly localized areas of interest in cell sample populations is compared to provide reliable and highly-sensitive information concerning the physiological state or condition of the sample population. High spatial resolution is provided, for example, by implementing high resolution cameras and charge coupled devices (CCDs). Apparatus suitable for obtaining such images have been described in the patents incorporated herein by reference.

Various data processing techniques may be advantageously used to assess the data collected in accordance with the present invention. Comparison data may be assessed or presented in a variety of formats. Processing may include averaging or otherwise combining a plurality of data sets to produce control, subsequent and various comparison data sets. Data may be converted from an analog to a digital form for processing, and back to an analog form for display as an image. Alternatively, data may be acquired, processed, analyzed, and output in a digital form.

Data processing may also include amplification of certain signals or portions of a data set (e.g., areas of an image) to enhance the contrast seen in data set comparisons, and to thereby identify cells or cell populations undergoing changes in geometrical and/or optical properties with a high degree of spatial resolution. For example, according to one embodiment, images are processed using a transformation in which image pixel brightness values are remapped to cover a broader dynamic range of values. A "low" value may be selected and mapped to zero, with all pixel brightness values at or below the low value set to zero, and a "high" value may be selected and mapped to a selected value, with all pixel brightness values at or above the high value mapped to the high value. Pixels having an intermediate brightness value, representing the dynamic changes in brightness indicative of neuronal activity, may be mapped to linearly or logarithmically increasing brightness values. This type of processing manipulation is frequently referred to as a "histogram stretch" and can be used according to the present invention to enhance the contrast of data sets, such as images, representing changes in neuronal activity.

Data processing techniques may also be used to manipulate data sets to provide more accurate combined and comparison data. For example, for in vivo applications, movement, respiration, heartbeat, seizure or reflex activity may shift an area of interest during data acquisition. It is important that corresponding data points in data sets are spatially resolved and precisely aligned to provide accurate combined and comparison data. Optical markers may be fixed at an area of interest and detected as the data is collected to aid in manual alignment or mathematical manipulation of data sets. Various processing techniques are described below and in the patents incorporated herein by reference.

Comparison data may be displayed in a variety of ways. Comparison data may be displayed, for example, in a graphical format that highlights geometrical or optical differences indicative of physiological changes. A preferred technique for presenting and displaying comparison data is in the form of visual images or photographic frames corresponding to spatially resolved areas of interest. This format provides a visualizable spatial location (two- or three-dimensional) of a cell population being analyzed. To enhance and provide better visualization of high contrast areas indicating changes in geometrical and/or optical properties indicative of physiological activity or dysfunction, comparison data may be processed to provide an enhanced contrast grey scale or even a color image. A look up table ("LUT") may be provided, for example, that converts the grey scale values for each pixel to a different (higher contrast) grey scale value, or to a color value. Color values may map to a range of grey scale values, or color may be used to distinguish between positive-going and negative-going geometrical or optical changes. In general, color-converted images provide higher contrast images that highlight changes in optical properties representing physiological activity, function or dysfunction.

Systems of the present invention generally comprise an illumination source for illuminating the biological material, an optical detector for acquiring data relating to a geometrical or optical property of the biological material, and data storage and analysis and output device(s) for storing data relating to a geometrical or optical property of the biological material, comparing various data sets, and/or control data profiles, to generate comparison data relating to changes in geometrical and/or optical properties indicative of changes in the physiological state of sample populations and to provide or display the output data in a useful format.

An emr source is used for illuminating an area of interest during acquisition of data representing one or more dimensional or intrinsic optical properties of cells or tissue at an area of interest. The emr source may be utilized to illuminate an area of interest directly, as when in vitro cell cultures maintained in optically transparent containers are illuminated or when tissue is exposed, such as in connection with surgery, or it may be utilized to illuminate an area of interest indirectly through adjacent or overlying tissue such as bone, dura, skin, muscle and the like. The emr source employed in the present invention may be a high or low intensity source, and may provide continuous or non-continuous illumination. Suitable illumination sources include high and intensity sources, broad spectrum and non-chromatic sources, tungsten-halogen lamps, lasers, light emitting diodes, and the like. Cutoff filters for selectively passing all wavelengths above or below a selected wavelength may be employed. A preferred cutoff filter excludes all wavelengths below about 695 nm.

Preferred emr wavelengths for acquiring data relating to intrinsic optical signals include, for example, wavelengths of from about 450 nm to about 2500 nm, and most preferably, wavelengths of the near infrared spectrum of from about 700 nm to about 2500 nm. Generally, longer wavelengths (e.g., approximately 800 nm) are employed to detect cellular or tissue condition of locations beneath the surface of cells or tissue, or beneath other materials such as skin, bone, dura, and the like, cortical activity. Selected wavelengths of emr may also be used, for example, when various types of contrast enhancing agents are administered. The emr source may be directed to the area of interest by any appropriate means. For some applications, the use of optical fibers is preferred. One preferred arrangement provides an emr source through strands of fiber optic using a beam splitter controlled by a D.C. regulated power supply (Lambda, Inc.).

The optical detection methods of the present invention may also usefully employ non-continuous illumination and detection techniques. For example, short pulse (time domain), pulsed time, and amplitude modulated (frequency domain) illumination sources may be used in conjunction with suitable detectors (see, Yodh, A. and Chance, B., *Physics Today*, March, 1995). Frequency domain illumination sources typically comprise an array of multiple source elements, such as laser diodes, with each element modulated at 180° out of phase with respect to adjacent elements (see, Chance, B. et al., *Proc. Natl. Acad. Sci. USA*, 90:3423–3427, 1993). Two-dimensional arrays, comprising four or more, elements in two orthogonal planes, can be employed to obtain two-dimensional localization information. Such techniques are described in U.S. Pat. Nos. 4,972,331 and 5,187,672 which are incorporated by reference herein in their entireties.

Time-of-flight and absorbance techniques (Benaron, D. A. and Stevenson, D. K., *Science* 259:1463–1466, 1993) may also be usefully employed in the present invention. In yet another embodiment of the present invention, a scanning laser beam may be used in conjunction with a suitable detector, such as a photomultiplier tube, to obtain high resolution data images, preferably in the form of an area of interest.

Illumination with a part of the infrared spectrum allows for detection of intrinsic optical signals through tissue overlying or adjacent the area of interest, such as dura and skull. One exemplary infrared emr source suitable for detection of intrinsic optical signals through tissue overlying or adjacent the area of interest is a Tunable IR Diode Laser from Laser Photonics, Orlando, Fla. When using this range of far infrared wavelengths, the optical detector is preferably provided as an infrared (IR) detector. IR detectors may be constructed from materials such as indium arsenide, germanium and mercury cadmium telluride, and are generally cryogenically cooled to enhance their sensitivity to small changes in infrared radiation. One example of an IR detection system which may be usefully employed in the present invention is an IRC-64 infrared camera (Cincinnati Electronics, Mason, Ohio).

The area of interest is preferably evenly illuminated to effectively adjust the signal over a full dynamic range, as described below. Nonuniformity of illumination is generally caused by fluctuations of the illumination source and intensity variations resulting from the three-dimensional nature of the tissue surface. More uniform illumination can be provided over the area of interest, for example, by using diffuse lighting, mounting a wavelength cutoff filter in front of the optimal detector and/or emr source, or combinations thereof. Fluctuation of the illumination source itself is preferably prevented by using a light feedback mechanism to regulate the power supply of the illumination source. In addition, a sterile, optically transparent plate may contact and cover an area of interest to provide a flatter, more even contour surface for detection. Fluctuations in illumination can be compensated for using detection processing algorithms, including placing a constant shade grey image marker point at the area of interest as a control point.

The system also comprises an optical detector for acquiring a signal representative of one or more optical properties of the area of interest. Any photon detector may be employed as an optical detector. Suitable optical detectors include, for example, photo diodes, photo multiplier tubes, photo sensitive silicon detector chips, such as those provided in CCD devices, and the like. Multiple emr sources and/or multiple photon detectors may be provided and may be arranged in any suitable arrangement. Specialized detectors for detecting selected optical properties may be employed. One preferred optical detector for acquiring data in the format of an analog video signal is a CCD video camera which produces an output video signal at 30 Hz having, for example, 512 horizontal lines per frame using standard RS 170 convention. One suitable device is a CCD-72 Solid State Camera (Dage- MTI Inc., Michigan City, Ind.). Another suitable device is a COHU 6510 CCD Monochrome Camera with a COHU 6500 electronic control box (COHU Electronics, San Diego, Calif.). In some cameras, the analog signal is digitized 8-bits deep on an ADI board; (analog-to-digital board). The CCD may be cooled, if necessary, to reduce thermal noise.

Data processing is an important feature of the optical detection and analysis techniques and systems of the present invention. In use, for example, a CCD apparatus is preferably adjusted (at the level of the analog signal and before digitizing) to amplify the signal and spread the signal across the full possible dynamic range, thereby maximizing the sensitivity of the apparatus. Specific methods for detecting optical signals with sensitivity across a full dynamic range are described in detail in the patents incorporated herein by reference. Means for performing a histogram stretch of the difference frames (e.g., Histogram/Feature Extractor HF 151-1-V module, Imaging Technology, Woburn, Mass.) may be provided, for example, to enhance each difference image across its dynamic range. Exemplary linear histogram stretches are described in Green, *Digital Image Processing: A Systems Approach*, Van Nostrand Reinhold: New York, 1983. A histogram stretch takes the brightest pixel, or one with the highest value in the comparison image, and assigns it the maximum value. The lowest pixel value is assigned the minimum value, and every other value in between is assigned a linear value (for a linear histogram stretch) or a logarithmic value (for a log histogram stretch) between the maximum and minimum values. This allows the comparison image to take advantage of the full dynamic range and provide a high contrast image that clearly identifies areas of neuronal activity or inactivity.

Noise (such as 60 Hz noise from A.C. power lines) is filtered out in the control box by an analog filter. Additional adjustments may further enhance, amplify and condition the analog signal from a CCD detector. One means for adjusting the input analog signal is to digitize this signal at video speed (30 Hz), and view the area of interest as a digitized image that is subsequently converted back to analog format.

It is important that data, such as consecutive data sets corresponding to a particular area of interest, be aligned so that data corresponding to the same spatially resolved location is compared. If data sets are misaligned prior to comparison, artifacts are introduced and the resulting comparison data set may amplify noise and edge information. Data misalignment may be caused by sample movement or motion, heartbeat, respiration, and the like. Large movements of cells in an area of interest being analyzed may require a new orientation of the detector. It is possible to compensate for small movements of cells in the area of interest by either mechanical or computational means, or a combination of both.

Real-time motion compensation and geometric transformations may also be used to align corresponding data. Simple mechanical translation of data or more complex (and generally more accurate) geometric transformation techniques can be implemented, depending upon the input data collection rate and amount and type of data processing. For many types of image data, it is possible to compensate by a geometrical compensation which transforms the images by translation in the x-y plane. In order for an algorithm such as this to be feasible, it must be computationally efficient (preferably implementable in integer arithmetic), memory efficient, and robust with respect to changes in ambient light.

For example, functional control points or numbers can be located in an area of interest and triangulation-type algorithms used to compensate for movements of these control points. Goshtasby ("Piecewise Linear Mapping Functions for Image Registration," *Pattern Recognition* 19:459–66, 1986) describes a method whereby an image is divided into triangular regions using control points. A separate geometrical transformation is applied to each triangular region to spatially register each control point to a corresponding triangular region in a control image.

"Image warping" techniques may be employed whereby each subsequent image is registered geometrically to the averaged control image to compensate for movement. Image warping techniques (described in, for example, Wolberg, *Digital Image Warping*, IEEE Computer Society Press: Los Alamitos, Calif., 1990), may be used. Image warping techniques can further indicate when movement has become too great for effective compensation and a new averaged control image must be acquired.

The data storage processing and analysis function is generally performed and controlled by a host computer. The host computer may comprise any general computer (such as an IBM PC type with an Intel 386, 486, Pentium or similar microprocessor or Sun SPARC) that is interfaced with the emr source and/or optical detector and controls data acquisition and flow, comparison computations, analysis, output, and the like. The host computer thus controls acquisition and analysis of data and provides a user interface.

The host computer may comprise a single-board embedded computer with a VME64 interface, or a standard (IEEE 1014-1987) VME interface, depending upon bus bandwidth considerations. Host computer boards which may be employed in the present invention include, for example, Force SPARC/CPU-2E and HP9000 Model 7471. The user interface can be, for example, a Unix/X-Window environment. The image processing board can be, for example, based upon Texas Instruments' MVP and other chips to provide real-time image averaging, registration and other processing necessary to produce high quality difference images for intraoperative viewing. This board will also drive a 120×1024 RGB display to show a sequence of difference images over time with pseudo color mapping to highlight tumor tissue. Preferably, a second monitor is used for the host computer to increase the overall screen real estate and smooth the user interface. The processing board (fully programmable) can support a VME64 master interface to control data transactions with the other boards. Lastly, a peripheral control board can provide electrical interfaces to control mechanical interfaces from the host computer. Such mechanical interfaces can include, for example, the light source and optical detector control box.

A real-time data acquisition and display system, for example, may comprise four boards for acquisition, image processing, peripheral control and host computer. A minimal configuration with reduced processing capabilities may comprise just the acquisition and host computer boards. The acquisition board comprises circuitry to perform real-time averaging of incoming video frames and allow readout of averaged frames at a maximum rate bus. A VME bus is preferred because of its high peak bandwidth and compatibility with a multitude of existing VME products. The acquisition board should also support many different types of optical detectors via a variable scan interface. A daughter board may support the interfacing needs of many different types of optical detectors and supply variable scan signals to the acquisition motherboard. Preferably, the unit comprises a daughter board interfacing to an RS-170A video signal to support a wide base of cameras. Other camera types, such as slow scan cameras with a higher spatial/contrast resolution and/or better signal to noise ratio, can be developed and incorporated in the inventive device, as well as improved daughter boards to accommodate such improved cameras.

Data relating to dimensional and/or intrinsic optical properties of a sample population acquired, for example, as analog video signals, may be continuously processed using, for example, an image analyzer (e.g., Series 151 Image Processor, Imaging Technologies, Inc., Woburn, Mass.). An image analyzer receives and digitizes an analog video signal with an analog to digital interface and performs at a frame speed of about $\frac{1}{30}$th of a second (e.g., 30 Hz or "video speed"). Processing the signal involves first digitizing the signal into a series of pixels or small squares assigned a value (in a binary system) dependent upon the number of photons (i.e., quantity of emr) being reflected off tissue from the part of the area of interest assigned to that pixel. For example, in a standard 512×512 image from a CCD camera, there would be 262,144 pixels per image. In an 8 bit system, each pixel is represented by 8 bits corresponding to one of 256 levels of grey.

The signal processor may include a programmable look-up table (e.g., CM150-LUT16, Imaging Technology, Woburn, Mass.) initialized with values for converting grey coded pixel values, representative of a black and white image, to color coded values based upon the intensity of each grey coded value. Using image stretching techniques, the highest and lowest pixel intensity values representing each of the pixels in a digital image frame are determined over a region of the image frame which is to be stretched. Stretching a selected region over a larger range of values permits, for example, easier identification and removal of relatively high, spurious values resulting from noise.

The signal processor means may further include a plurality of frame buffers having frame storage areas for storing frames of digitized image data received from the A/D interface. The frame storage area comprises at least one megabyte of memory space, and preferably at least 8 megabytes of storage space. An additional 16-bit frame storage area may be provided as an accumulator for storing processed image frames having pixel intensities represented by more than 8 bits. The processor means preferably includes at least three frame buffers, one for storing the averaged control image, another for storing the subsequent image, and a third for storing a comparison image.

The signal processor may further comprise an arithmetic logic unit (e.g., ALU-150 Pipeline Processor) for performing arithmetical and logical functions on data located in one or more frame buffers. An ALU may, for example, provide image (data) averaging in real time. A newly acquired digitized image may be sent directly to the ALU and combined with control images stored in a frame buffer. A 16 bit result can be processed through an ALU, which will divide this result by a constant (i.e., the total number of images). The output from the ALU may be stored in a frame buffer, further processed, or used as an input and combined with another image.

Normally, areas of increased physiological activity exhibit an increase of the emr absorption capacity of the cell sample or tissue (i.e., the cell sample get darker if visible light is used for emr illumination, or an intrinsic signal increases in a positive direction). Similarly, a reduction in physiological activity generally corresponds to a decrease of emr absorption capacity of the tissue (i.e., the tissue appears brighter, or intrinsic signals become negative). For example, data set A is a subsequent averaged image and data set B is an averaged control image. Normally, when a pixel in data set A is subtracted from a pixel in data set B and a negative value results, this value is treated as zero. Hence, difference images cannot account for areas of inhibition. The present invention provides a method for identifying both negative and positive intrinsic signals, by: (a) subtracting data set A (a subsequent averaged image) from data set B (an averaged control image) to create a first difference data set, whereby all negative pixel values are zero; and (b) subtracting data set B from data set A to create a second difference data set whereby all negative pixel values are zero; and adding the first and second difference data sets to create a "sum difference data set." The sum difference data set shows areas of increased activity (i.e., color coded with warmer colors such as yellow, orange, red) and may be visualized as image areas of less activity or inhibition (i.e., color coded with colder colors such as green, blue, purple). Alternatively, one can overlay the first difference data set on the second difference data set. The difference output may be visualized as an image and may be superimposed on the real time analog image to provide an image of the area of interest (e.g., cortical surface) superimposed with a color-coded difference frame to indicate where there are intrinsic signals in response to a challenge, stimulus, paradigm, or the like.

The comparison (e.g., difference) data may be further processed to smooth out the data and remove high frequency noise. For example, a lowpass spatial filter can block high spatial frequencies and/or low spatial frequencies to remove high frequency noises at either end of the dynamic range. This provides a smoothed-out processed difference data set (in digital format). The digitally processed difference data set can be provided as an image and color-coded by assigning a spectrum of colors to differing shades of grey. This image may then be converted back to an analog image (by an ADI board) and displayed. for a real time visualization of differences between an averaged control image and subsequent images. Moreover, the processed difference image can be superimposed over the analog image to display specific tissue sites where a contract enhancing agent may have a faster uptake, or where an intrinsic signal may be occurring.

Processing speed may be enhanced by adding a real time modular processor or faster CPU chip to the image processor. One example of a real time modular processor which may be employed in the present invention is a 150 RTMP-150 Real Time Modular Processor (Imaging Technology, Woburn, Mass.). The processor may further include an optical disk for storing digital data, a printer for providing a hard copy of the digital and/or analog data and a display, such as a video monitor, to permit the user to continuously monitor the comparison data output.

A single chassis may house all of the modules necessary to provide, optical detection and analysis in a format that can be easily interpreted, such as an image format, according to the present invention. The necessary components, whether or to whatever degree integrated, may be installed on a rack that is easily transportable, along with display monitors and peripheral input and output devices.

A preferred high resolution and high performance system comprising a PentaMAX 576×384FT LCD system (by Princeton Instruments Inc., N.J.) digitizes the data at the chip and provides a large dynamic range and reduced noise. This system may be interfaced using a PCI-bus to a dual-400 Mhz Pentium PC running windows NT. Image analysis algorithms may be written in C using Microsoft VisualC++ Version 5.0 compiler. For more rapid online processing, the data may be routed to dedicated imaging hardware residing in the PC computer. For example, IM-PCI hardware (by Imaging Technology Inc., Bedford, Mass.) could be used. One such configuration would consist of the following IM-PCI boards and modules: IM-PCI, AMVS, and a CMALU.

The imaging methods applied to in vivo applications may acquire data at the surface of an area of interest. As described in the patents incorporated herein by reference, longer wavelengths of emr (in the infrared range) can be used to image areas of interest which are deeper in tissue or below overlying tissue. In some areas of the body, longer wavelength visible light and near infrared emr can easily pass through such tissue for imaging. Moreover, if a difference image is created between images acquired at two different illumination wavelengths, such as an image acquired at 500 nm emr and an image acquired at 700 nm emr, the difference image represents an optical slice of tissue. Additionally, administration of an imaging agent which absorbs specific wavelengths of emr can act as a filter in the area of interest. In this instance, it is desirable to utilize an imaging agent that remains in the tissue for a prolonged period of time.

In a simple system suitable for assessing cell populations in situ in animal or tissue culture models, the systems of the present invention may include one or more optical fiber(s) operably connected to an emr source that illuminates cells or tissue, and another optical fiber operably connected to an optical detector, such as a photodiode, that detects one or more optical properties of the illuminated cells or tissue. The detector may be used to acquire control data representing the "normal" or "background" optical properties of a sample population, and then to acquire subsequent data representing the optical properties of the sample population during or following administration of a test agent or test condition. A physiological challenge and/or a stimulus that stimulates a disease or pathological state may be administered prior to administration of the treatment agent or condition. The system comprises or is in communication with a data storage and processing system having information storage and processing capability sufficient to compare the geometrical and/or optical properties of individual cells or cell samples to empirically determined standards, or to data acquired at different points in time.

In operation, an area of interest in an in vitro or in vivo cell sample is illuminated with electromagnetic radiation (emr) and one or a series of data points or data sets representing one or more geometrical and/or optical properties of a spatially resolved area of interest is acquired during an interval of "normal" physiological activity. This data represents a control, or background data profile for that particular cell sample under those particular physiological conditions. A series of data sets is preferably combined, for example by averaging, to obtain a control data profile. The control data profile is stored for comparison with other data sets. Similarly, control data sets may be collected and stored that represent a background data profile for particular cell types under specified physiological conditions.

Data sets representing the corresponding geometrical and/or optical property of the sample population at the same, spatially resolved areas of interest, are acquired during a subsequent time period. For monitoring applications, data may be collected at regular time intervals to monitor the condition of the cell sample and to detect aberrations from the baseline profile. For screening applications, one or more subsequent data, set(s) is collected during a period following physiological activity or inhibition, induced, for example, by introduction of a test compound or by exposure to a test condition. Physiological activity or inhibition may be induced by a "natural" occurrence such as a seizure or stroke in an animal model, or it may be induced by administering a paradigm or an agent to an in vitro or in vivo cell sample to stimulate changes in geometrical and/or optical properties of the cell sample that are indicative of physiological activity or inhibition. During a monitoring interval or stimulation of an intrinsic physiological response, one or a series of subsequent data sets, representing one or more of the detected geometrical or optical properties of the area of interest, is acquired. A series of subsequent data sets is preferably combined, for example by averaging, to obtain a subsequent data set. The subsequent data set is compared with the control data set to obtain a comparison data set, preferably a difference data set. Comparison data sets are then analyzed for evidence of changes in geometrical and/or optical properties representative of physiological activity or inhibition within the area of interest.

A cell population may comprise cells in suspension at a sparse cell density, or confluent layers of cells, or layers of cells at other predetermined cell densities, or a tissue sample, such as a tissue slice. Maintenance of a wide variety of cell and tissue samples under cell culture conditions is well known in the art.

The sample population is placed at a predetermined location on a platform, such as on a microscope stage. One exemplary tissue sample is an acute rat hippocampal slice maintained in a submerged perfusion chamber. Alternatively, the sample may be cell samples maintained in cell culture media in flasks, multiple well plates, and the like. Multiple well tissue culture plates may be used for high throughput screening, in combination with an automated stage for positioning cell samples in individual wells for optical detection at predetermined intervals. Programmable, automated positioning devices are well known in the art.

An optical detector (such as a CCD camera) is attached to the camera-port of the microscope. During one or more control period(s) and one or more test period(s), data relating to dimensional and/or optical properties of individual cells or of an area of interest in the cell sample are acquired, stored and processed. Acquisition and processing of data may be accomplished as described below and in the Examples.

The grey-scale image on the upper right is the unprocessed image of the tissue-slice as viewed by the CCD camera. The tissue slice may then be electrically stimulated at two different intensities: a low-intensity electrical stimulus causing small increase in neuronal and synaptic activation; and a high-intensity electrical stimulus causing a larger increase in neuronal and synaptic activity.

A pseudo-colored image maybe generated as described above. Briefly, an image acquired during the electrical stimulation maybe subtracted from an image acquired in the control state. This image was then filtered with a low-pass filter, histogram-stretched, and pseudo-colored. The colors can be coded to indicate intensity of activity-evoked optical change.

The dynamic optical changes represented in the images produced as described above can also be plotted as a graph. In graphical form, each data-point represents the average change in light-transmission through unite indicated on the pseudo-colored image. A series of images, separated in time intervals, may be acquired and the average value calculated for each image and plotted as a point on the graph. The tissue was electrically stimulated for two seconds at the points indicated by the straight lines. The small peak indicates the maximum optical change induced by the first small electrical stimulation, the larger peak from the second larger stimulus. The electrical stimulation was ceased after two seconds and the tissue was allowed to recover. The plots of the recovery are characteristic of the ion-homeostatic mechanisms of the tissue. Their recovery could be quantified, for example, by finding the best exponential fits for the recovery periods.

Candidate compounds may be screened for chloride cotransporter agonist and/or antagonist activity using screening methods of the present invention with various types of cells in culture such as glial cells, neuronal cells, renal cells, and the like, or in situ in animal models. Screening techniques to identify chloride cotransporter antagonist activity, for example, may involve altering the ionic balance of the extracellular space in the tissue culture sample, or in situ in an animal model, by producing a higher than "normal" anionic chloride concentration. The geometrical and/or optical properties of the cell or tissue sample subject to this altered ionic balance are determined, and candidate agents are administered. Following administration of the candidate agents, the corresponding geometrical and/or optical properties of the cell or tissue sample are monitored to determine whether the ionic imbalance remains, or whether the cells responded by altering the ionic balances in the extracellular and intracellular space. If the ionic imbalance remains, the candidate agent is likely a chloride cotransporter antagonist. By screening using various types of cells or tissues, candidate compounds having a high level of glial cell chloride cotransporter antagonist activity and having a reduced level of neuronal cell and renal cell chloride cotransporter antagonist activity may be identified. Similarly, effects on different types of cells and tissue systems may be assessed.

Additionally, the efficacy of candidate compounds for treating various conditions of the central and peripheral nervous system may be assessed by simulating or inducing a condition, such as a seizure, central nervous system edema, ethanol neurotoxicity, cortical spreading depression, or the like, in a tissue sample or in situ in an animal model, monitoring the geometrical and/or optical properties of the cell or tissue sample during stimulation of the condition, administering the candidate compound, then monitoring the geometrical and/or optical properties of the cell or tissue sample following administration of the candidate compound, and comparing the geometrical and/or optical properties of the cell or tissue sample to determine the effect of the candidate compound. Similarly, the efficacy of treatment composition(s) in an animal or human subject may be monitored in situ using the optical methods and systems of the present invention.

The treatment compositions and methods of the present invention have been described, above, with respect to certain preferred embodiments. The Examples set forth below describe the results of specific experiments and are not intended to limit the invention in any fashion.

EXAMPLE 1

The Effects of Furosemide on Epileptiform Discharges Hippocampal Slices

During these studies, spontaneous epileptiform activity was elicited by a variety of treatments. Sprague-Dawley rats (males and females; 25–35 days old) were decapitated, the top of the skull was rapidly removed, and the brain chilled with ice-cold oxygenated slicing medium. The slicing medium was a sucrose-based artificial cerebrospinal fluid (sACSF) consisting of 220 mM sucrose, 3 mM KCl, 1.25 mM $NaH_2PO_4$, 2 MM $MgSO_4$, 26 mM $NaHCO_3$, 2 mM $CaCl_2$, and 10 mM dextrose (295–305 mOsm). A hemisphere of brain containing hippocampus was blocked and glued (cyanoacrylic adhesive) to the stage of a Vibroslicer (Frederick Haer, Brunsick, Me.). Horizontal or transverse slices 400 µm thick were cut in 4° C., oxygenated (95% $O_2$; 5% $CO_2$) slicing medium. The slices were immediately transferred to a holding chamber where they remained submerged in oxygenated bathing medium (ACSF) consisting of 124 mM NaCl, 3 mM KCl, 1.25 mM $NaH_2PO_4$, 2 mM $MgSO_4$, 26 mM $NaHCO_3$, 2 mM $CaCl_2$, and 10 mM dextrose (295–305 mOsm). The slice were held at room temperature for at least 45 minutes before being transferred to submersion-style recording chamber (all other experiments). In the recording chamber, the slices were perfused with oxygenated recording medium at 34–35° C. All animal procedures were conducted in accordance with NIH and University of Washington, animal care guidelines.

In most slice experiments, simultaneous extracellular field electrode recordings were obtained from CA1 and CA3 areas. A bipolar tungsten stimulating electrode was placed on the Schaffer collaterals to evoke synaptically-driven field responses in CA1. Stimuli consisted of 100–300 sec duration pulses at an intensity of four times the, population-spike threshold. After discharges were evoked by a 2 second train of such stimuli delivered at 60 Hz. Spontaneous interictal-like bursts were observed in slices treated by the following modifications or additions to the bathing medium: 10 mM potassium (6 slices; 4 animals; average—81 bursts/min.); 200–300 M 4-aminopyridine (4 slices; 2 animals; average—33 burst/min.); 50–100 M bicuculline (4 slices; 3 animals; average—14 bursts/min); ) [?]M $Mg^{++}$ (1 hour of perfusion—3 slices; 2 animals; average—20 bursts/min. or 3 hours of perfusion—2 slices; 2 animals); zero calcium/6 mM KCl and 2 mM EGTA (4 slices; 3 animals). In all treatments, furosemide was added to the recording medium once a consistent level of bursting was established.

In the first of these procedures, episodes of after discharges were evoked by electrical stimulation of the Schaffer collaterals (Stasheff et al., *Brain Res.* 344:296, 1985) and the extracellular field response was monitored in the CA1 pyramidal cell region (13 slices; 8 animals). The concentration of $Mg^{++}$ in the bathing medium was reduced to 0.9 mM and after discharges were evoked by stimulation at 60 Hz for 2 seconds at an intensity 4 times the population spike threshold (population spike threshold intensity varied between 20–150 µA at 100–300 µsec pulse duration). The tissue was allowed to recover for 10 minutes between stimulation trials. In each experiment, the initial response of CA1 to synaptic input was first tested by recording the field potential evoked by a single stimulus pulse. In the control condition, Schaffer collateral stimulation evoked a single population spike (FIG. 1A, inset). Tetanic stimulation evoked approximately 30 seconds after, discharge (FIG. 1A, left) associated with a large change in intrinsic signal (FIG. 1A, right).

For imaging of intrinsic optical signals, the tissue was placed in a perfusion chamber located on the stage of an upright microscope and illuminated with a beam of white light (tungsten filament light and lens system—Dedo Inc.) directed through the microscope condenser. The light was controlled and regulated (power supply-Lamdar Inc.) to minimize fluctuations and filtered (695 nm longpass) so that the slice was transilluminated with long wavelengths (red). Field of view and magnification were determined by the choice of microscope objectives (4× for monitoring the entire slice). Image-frames were acquired with a charge-coupled device (CCD) camera (Dage MTI Inc.) at 30 HZ and were digitized at 8 bits with a spatial resolution of 512×480 pixels using an Imaging Technology Inc. Series 151 imaging system; gains and offsets of the camera-control box and the, A/D board were adjusted to optimize the sensitivity of the system. Imaging hardware was controlled by a 486-PC compatible computer. To increase signal/noise, an averaged-image was composed from 16 individual image-frames, integrated over 0.5 sec and averaged together. An experimental series typically involved the continuous acquisition of a series of averaged-images over a several minute time period; at least 10 of these averaged-images were acquired as control-images prior o stimulation. Pseudocoloured images were calculated by subtracting the first control-image from subsequently acquired images and assigning a color lookup table to the pixel values. For these images, usually a linear low-pass filter was used to remove high frequency noise and a linear-histogram stretch was used to map the pixel values over the dynamic range of the system. All operations on these images were linear so that quantitative information was preserved. Noise was defined as the maximum standard deviation of fluctuations of AR/R of the sequence of control images within a given acquisition series, where AR/R represented the magnitude of the change in light-transmission through the tissue. Delta R/R was calculated by taking all the difference-images and dividing by the first control image: (subsequent image—first-control-image)/first-control-image. The noise was always <0.01 for each of the chosen image sequences. The absolute change in light transmission through the tissue was estimated during some experiments by acquiring images after placing neutral density filters between the camera and the light source. On average, the camera electronics and imaging system electronics amplified the signal 10-fold prior to digitization so that the peak absolute changes in light transmission through the tissue were usually between 1% and 2%.

The gray-scale photo shown in FIG. 1D is a video image of a typical hippocampal slice in the recording chamber. The fine gold-wire mesh that was used to hold the tissue in place can be seen as dark lines running diagonally across the slice. A stimulating electrode can be seen in the upper right on the stratum radiatum of CA1. The recording electrode (too thin to be seen in the photo) was inserted at the point indicated by the white arrow. FIG. 1A illustrates that two seconds of stimulation at 60 Hz elicited after discharge activity and shows a typical after discharge episode recorded by the extracellular electrode. The inset of FIG. 1A shows the CA1 field response to a single 200 sec test pulse (artifact at arrow) delivered to the Schaffer collaterals. FIG. 1A1 shows a map of the peak change in optical transmission through the tissue evoked by Schaffer collateral stimulation. The region of maximum optical change corresponds to the apical and basal dendritic regions of CA1 on either side of the stimulating electrode. FIG. 1B illustrates sample traces showing responses to stimulation after 20 minutes of perfusion with medium containing 2.5 mM furosemide. Both the electrical after discharge activity (shown in FIG. 1B) and the stimulation-evoked optical changes (shown in FIG. 1B1) were blocked. However, there was a hyper-excitable field response (multiple population spikes) to the test pulse (inset). FIGS. 1C and 1C1 illustrate that restoration of initial response patterns was seen after 45 minutes of perfusion with normal bathing medium.

The opposing effects of furosemide-blockade of the stimulation-evoked after discharges and a concomitant increase of the synaptic response to a test-pulse illustrate the two key results: (1) furosemide blocked epileptiform activity, and (2) synchronization (as reflected by spontaneous epileptiform activity) and excitability (as reflected by the response to a single synaptic input) were dissociated. Experiments in which the dose-dependency of furosemide was examined determined that a minimum concentration of 1.25 mM was required to block both the after discharges and optical changes.

EXAMPLE 2

Figure 2B:
Figure 2C:
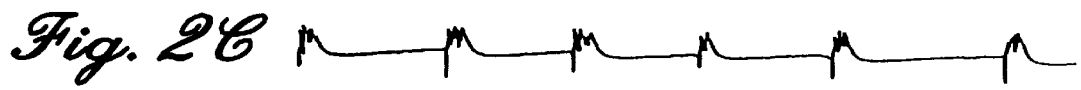
Figure 2D:
Figure 2E:
Figure 2F:
Figure 2G:
Figure 2H:
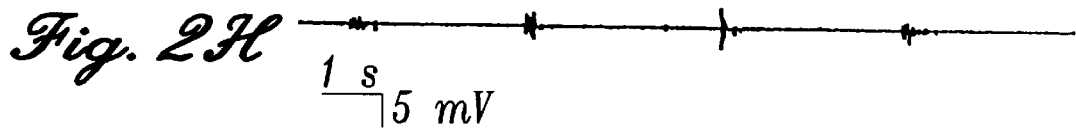

The Effects of Furosemide on Epileptiform Discharges in Hippocampal Slices Perfused with High-$K^+$ (10 mM) Bathing Medium Rat hippocampal slices prepared as described above, were perfused with a high-$K^+$ solution until extended periods of spontaneous interictal-like bursting were recorded simultaneously in CA3 (top traces) and CA1 (lower traces) pyramidal cell regions (FIGS. 2A and 2B). After 15 minutes of perfusion with furosemide-containing medium (2.5 mM furosemide), the burst discharges increased in magnitude (FIGS. 2C and 2D). However, after 45 minutes of furosemide perfusion, the bursts were blocked in a reversible manner (FIGS. 2E, 2F, 2G and 2H). During this entire sequence of furosemide perfusion, the synaptic response to a single test pulse delivered to the Schaffer colalterals was either unchanged or enhanced (data not shown). It is possible that the initial increase in discharge amplitude reflected a furosemide-induced decrease in inhibition (Misgeld et al., *Science* 232:1413, 1986; Thompson et al., *J. Neurophysiol.* 60:105, 1988; Thompson and Gahwiler, *J. Neuropysiol.* 61:512, 1989; and Pearce, *Neuron* 10:189, 1993). It has previously been reported (Pearce, *Neuron* 10:189, 1993) that furosemide blocks a component of the inhibitory currents in hippocampal slices with a latency (<15 min.) similar to the time to onset of the increased excitability observed here. The longer latency required for the furosemide-block of the spontaneous bursting might correspond to additional time required for a sufficient block of the furosemide-sensitive cellular volume regulation mechanisms under high-$K^+$ conditions.

Figure 2I:
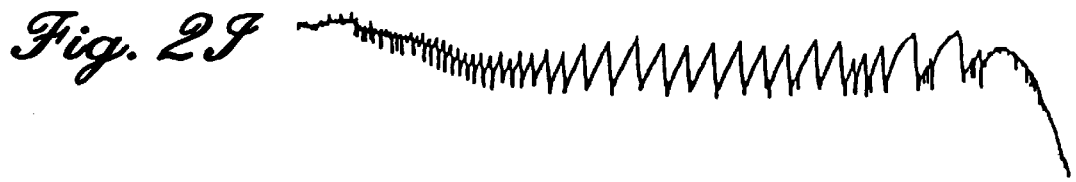
Figure 2J:
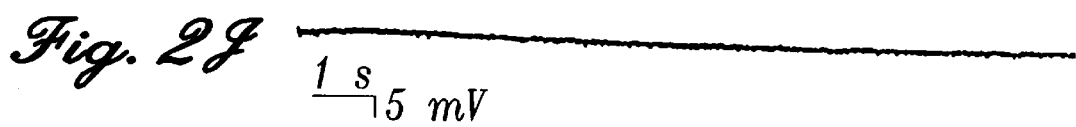
Figure 2K:
Figure 2L:
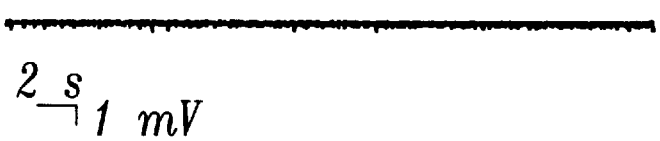
Figure 2M:
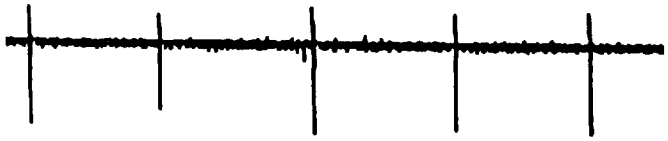
Figure 2N:
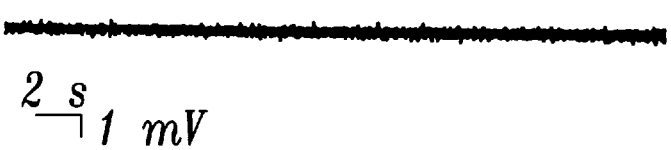
Figure 2O:
Figure 2P:
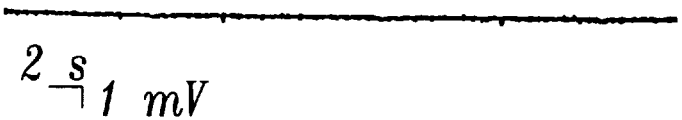
Figure 2Q:
Figure 2R:

After testing the effects of furosemide on slices perfused with high-$K^+$, similar studies were performed with a variety of other commonly studied in vitro models of epileptiform discharge (Galvan et al., *Brain Res.* 241:75, 1982; Schwartzkroin and Prince, *Brain Res.* 183:61, 1980; Anderson et al., *Brain Res.* 398:215, 1986; and Zhang et al., *Epilepsy Res.* 20:105, 1995). After prolonged exposure (2–3 hours) to magnesium-free medium (0-$Mg^{++}$), slices have been shown to develop epileptiform discharges that are resistant to common clinically used anticonvulsant drugs (Zhang et al., *Epilepsy Res.* 20:105, 1995). Recordings from entorhinal cortex (FIG. 2I) and subiculum (not shown) showed that after 3 hours of perfusion with 0-$Mg^{++}$ medium, slices developed bursting patterns that appeared similar to these previously described "anticonvulsant resistant" bursts. One hour after the addition of furosemide to the bathing medium, these bursts were blocked (FIG. 2J). Furosemide also blocked spontaneous burst discharges observed with the following additions/modifications to the bathing medium: (1) addition of 200–300 $\mu$M 4-aminopyridine (4-AP; a potassium channel blocker) (FIGS. 2K and 2L); (2) addition of the GABA antagonist, bicuculline, at 50–100 $\mu$M (FIGS. 2M and 2N); (3) removal of magnesium (0-$Mg^{++}$)—1 hours perfusion (FIGS. 2O and 2P); and (4) removal of calcium plus extracellular chelation (0-$Ca^{++}$) (FIGS. 2Q and 2R). With each of these manipulations, spontaneous interictal-like patterns were simultaneously recorded from CA1 and CA3 subfields (FIGS. 2K, 2L, 2M and 2N show only the CA3 trace and FIGS. 2O, 2P, 2Q, and 2R show only the CA1 trace). In the 0-$Ca^{++}$ experiments, 5 mM furosemide blocked the bursting with a latency of 15–20 minutes. For all other protocols, bursting was blocked by 2.5 mM furosemide with a latency of 20–60 minutes. Furosemide reversibly blocked the spontaneous bursting activity in both CA1 and CA3 in all experiments (FIGS. 2L, 2N, 2P and 2R).

EXAMPLE 3

The Effects of Furosemide on Epileptiform Activity Induced by i.v. Injection of Kainic Acid in Anesthetized Rats This example illustrates an in vitro model in which epileptiform activity was induced by i.v. injection of kainic acid (KA) into anesthetized rats (Lothman et al., *Neurology* 31:806, 1981). The results are illustrated in FIGS. 3A–3H. Sprague-Dawley rats (4 animals; weights 250–270 g) were anesthetized with urethane (1.25 g/kg i.p.) and anesthesia maintained by additional urethane injections (0.25 g/kg i.p.) as needed. Body temperature was monitored using a rectal temperature probe and maintained at 35–37° C. with a heating pad; heart rate (EKG) was continuously monitored. The jugular vein was cannulated on one side for intravenous drug administration. Rats were placed in a Kopf stereotaxic device (with the top of the skull level), and a bipolar stainless-steel microelectrode insulated to 0.5 mm of the tip was inserted to a depth of 0.5–1.2 mm from the cortical surface to record electroencephalographic (EEG) activity in the fronto-parietal cortex. In some experiments, a 2M NaCl-containing pipette was lowered to a depth of 2.5–3.0 mm to record hippocampal EEG. Data were stored on VHS videotape and analyzed off-line.

Following the surgical preparation and electrode placement, animals were allowed to recover for 30 minutes before the experiments were initiated with an injection of kainic acid (10–12 mg/kg i.v.). Intense seizure activity, an increased heart rate, and rapid movements of the vibrissae were induced with a latency of about 30 minutes. Once stable electrical seizure was evident, furosemide was delivered in 20 mg/kg boluses every 30 minutes to a total of 3 injections. Experiments were terminated with the intravenous administration of urethane. Animal care was in accordance with NIH guidelines and approved by the University of Washington Animal Care Committee.

FIGS. 3A–3H show furosemide blockade of kainic acid-evoked electrical "status epilepticus" in urethane-anesthetized rats. EKG recordings are shown as the top traces and EEG recordings are shown as the bottom traces. In this model, intense electrical discharge (electrical "status epilepticus") was recorded from the cortex (or from depth hippocampal electrodes) 30–60 minutes after KA injection (10–12 mg/kg) (FIGS. 3C and 3D). Control experiments (and previous reports, Lothman et al., Neurology, 31:806, 1981) showed that this status-like activity was maintained for well over 3 hours. Subsequent intravenous injections of furosemide (cumulative dose: 40–60 mg/kg) blocked seizure activity with a latency of 30–45 minutes, often producing a relatively flat EEG (FIGS. 3E, 3F, 3G and 3H). Even 90 minutes after the furosemide injection, cortical activity remained near normal baseline levels (i.e., that observed prior to the KA and furosemide injections). Studies on the pharmacokinetics of furosemide in the rat indicate that the dosages used in this example were well below toxic levels (Hammarlund and Paalzow, Biopharmaceutics Drug Disposition, 3:345, 1982).

Experimental Methods for Examples 4–7

Hippocampal slices were prepared from Sprague-Dawley adult rats as described previously. Transverse hippocampal slices 100 µm thick were cut with a vibrating cutter. Slices typically contained the entire hippocampus and subiculum. After cutting, slices were stored in an oxygenated holding chamber at room temperature for at least one hour before recording. All recordings were acquired in an interface type chamber with oxygenated (95% $O_2$, 5%$CO_2$) artificial cerebral spinal fluid (ACSF) at 34°–35° C. Normal ACSF contained (in mmol/l): 124 NaCl, 3 KCl, 1.25 $NaH_2PO_4$, 1.2 $MgSO_4$, 26 $NaHCO_3$, 2 $CaCl_2$, and 10 dextrose.

Sharp-electrodes for intracellular recordings from CA1 and CA3 pyramidal cells were filled with 4 M potassium acetate. Field recordings from the CA1 and CA3 cell body layers were acquired with low-resistance glass electrodes filled with 2 M NaCl. For stimulation of the Schaffer collateral or hilar pathways, a small monopolar tungsten electrode was placed on the surface of the slice. Spontaneous and stimulation-evoked activities from field and intracellular recordings were digitized (Neurocorder, Neurodata Instruments, New York, N.Y.) and stored on videotape. AxoScope software (Axon Instruments) on a personal computer was used for off-line analysis of data.

In some experiments, normal or low-chloride medium was used containing bicuculline (20 µM), 4-amino pyridine (4-AP) (100 µM), or high-$K^+$ (7.5 or 12 mM). In all experiments, low-chloride solutions (7, and 21 mM $[Cl^-]_o$) were prepared by equimolar replacement of NaCl with $Na^+$-gluconate (Sigma). All solutions were prepared so that they had a pH of approximately 7.4 and an osmolarity of 290–300 mOsm at 35° C. and at equilibrium from carboxygenation with 95%$O_2$/5%$CO_2$.

After placement in the interface chamber, slices were superfused at approximately 1 ml/min. At this flow-rate, it took 8–10 minutes for changes in the perfusion media to be completed. All of the times reported here have taken this delay into account and have an error of approximately 2 minutes.

EXAMPLE 4

Timing of Cessation of Spontaneous Epileptiform Bursting in Areas in CA1 and CA3

The relative contributions of the factors that modulate synchronized activity vary between areas CA1 and CA3. These factors include differences in the local circuitry and region-specific differences in cell packing and volume fraction of the extracellular spaces. If the anti-epileptic effects of anion or chloride-cotransport antagonisin are due to a desynchronization in the timing of neuronal discharge, chloride-cotransport blockade might be expected to differentially affect areas CA1 and CA3. To test this, a series of experiments was performed to characterize differences in the timing of the blockade of spontaneous epileptiform activity in areas CA1 and CA3.

Field activity was recorded simultaneously in areas CA1 and CA3 (approximately midway between the most proximal and distal extent the CA3 region), and spontaneous bursting was induced by treatment with high-$[K^+]_o$ (12 µM; n=12), bicuculline (20 mM; n=12), or 4-AP (100 µM; n=5). Single electrical stimuli were delivered to the Schaffer collaterals, midway between areas CA1 and CA3, every 30 seconds so that the field responses in areas CA1 and CA3 could be monitored throughout the duration of each experiment. In all experiments, at least 20 minutes of continuous spontaneous epileptiform bursting was observed prior to switching to low $[Cl^-]_o$ (21 mM) or furosemide-containing (2.5 mM) medium.

In all cases, after 30–40 minutes exposure to furosemide or low-chloride medium, spontaneous bursting ceased in area CA1 before the bursting ceased in area CA3. The temporal sequence of events typically observed included an initial increase in burst frequency and amplitude of the spontaneous field events, then a reduction in the amplitude of the burst discharges which was more rapid in CA1 than in CA3. After CA1 became silent, CA3 continued to discharge for 5–10 minutes, until it too no longer exhibited spontaneous epileptiform events.

This temporal pattern of burst cessation was observed with all epileptiform-inducing treatments tested, regardless of whether the agent used for blockade of spontaneous bursting was furosemide or low-$[Cl^-]_o$ medium. Throughout all stages of these experiments, stimulation of the Schaffer collaterals evoked hyperexcited field responses in both the CA1 and CA3 cell body layers. Immediately after spontaneous bursting was blocked in both areas CA1 and CA3, hyperexcited population spikes could still be evoked.

We considered the possibility that the observed cessation of bursting in CA1 prior to CA3 was an artifact of the organization of synaptic contacts between these areas relative to our choice of recording sites. It is known that the projections of the various subregions of CA3 terminate in an organized fashion in CA1; CA3 cells closer to the dentate gyrus (proximal CA3) tend to project most heavily to the distal portions of CA1 (near the subicular border), whereas CA3 projections arising from cells located more distally in CA3 terminate more heavily in portions of CA1 located closer to the CA2 border. If the cessation of bursting occurs in the different subregions of CA3 at different times, the results of the above set of experiments might arise not as a difference between CA1 and CA3, but rather as a function of variability in bursting activity across CA3 subregions. We tested this possibility in three experiments. Immediately after the spontaneous bursting ceased in CA1, we surveyed the CA3 field with a recording electrode. Recordings form several different CA3 locations (from the most proximal to the most distal portions of CA3), showed that all subregions of area CA3 were spontaneously bursting during this time that CA1 was silent.

The observation that CA3 continued to discharge spontaneously after CA1 became silent was unexpected since population discharges in CA3 are generally thought to evoke discharges in CA1 through excitatory synaptic transmission. As previously described, single-pulse stimuli delivered to the Schaffer collaterals still evoked multiple population spikes in CA1 even after the blockade of spontaneous bursting; thus, hyperexcited excitatory synaptic transmissions in CA3-to-CA1 synapse was intact. Given this maintained efficacy of synaptic transmission, and the continued spontaneous field discharges in CA3, we postulated that the loss of spontaneous bursting in CA1 was due to a decrease in synchronization of incoming excitatory drive. Further, since spontaneous epileptiform discharge in CA3 also eventually ceased, perhaps this desynchronization process occurred at different times in the two hippocampal subfields.

EXAMPLE 5

Effect of Chloride-cotransport Antagonism on the Synchronization of CA1 and CA3 Field Population Discharges The observation from Example 4 suggested a temporal relationship between the exposure time to low-$[Cl^-]_o$ or furosemide-containing medium and the characteristics of the spontaneous burst activity. Further, this relationship was different between areas CA1 and CA3. In order to better characterize the temporal relationships, we compared the occurrences of CA1 action potentials and the population spike events in the field responses of CA1 and CA3 subfields during spontaneous and stimulation-evoked burst discharge.

Intracellular recordings were obtained from CA1 pyramidal cells, with the intracellular electrode placed close (<100 μM) to the CA1 field electrode. The slice was stimulated every 20 seconds with single stimuli delivered to the Schaffer collaterals. After continuous spontaneous bursting was established for at least 20 minutes, the bathing medium was switched to bicuculline-containing low-$[Cl^-]_o$ (21 mM) medium. After approximately 20 minutes, the burst frequency and amplitude was at its greatest. Simultaneous field and intracellular recordings during this time showed that the CA1 field and intracellular recordings were closely synchronized with the CA3 field discharges. During each spontaneous discharge, the CA3 field response preceded the CA1 discharge by several milliseconds. During stimulation-evoked events, action potential discharges of the CA1 pyramidal cell were closely synchronized to both CA3 and CA1 field discharges.

With continued exposure to low-$[Cl^-]_o$ medium, the latency between the spontaneous discharges of areas CA1 and CA3 increased, with a maximum latency of 30–40 milliseconds occurring after 30–40 minutes exposure to the bicuculline-containing low-chloride medium. During this time, the amplitude of both the CA1 and CA3 spontaneous field discharges decreased. Stimulation-evoked discharges during this time closely mimicked the spontaneously occurring discharges in morphology and relative latency. However, the initial stimulus-evoked depolarization of the neuron (presumably, the monosynaptic EPSP) began without any significant increase in latency. The time interval during which these data were acquired corresponds to the time immediately prior to the cessation of spontaneous bursting in CA1.

After 40–50 minutes perfusion with low-$[Cl^-]_o$ medium, the spontaneous bursts were nearly abolished in CA1 but were unaffected in CA3. Schaffer collateral stimulation during this time showed that monosynaptically-triggered responses of CA1 pyramidal cells occurred without any significant increase in latency, but that stimulation-evoked field responses were almost abolished. The time interval during which these data were acquired corresponds to the moments immediately prior to the cessation of spontaneous bursting in CA3.

After prolonged exposure to low-$[Cl^-]_o$ medium, large increases (>30 milliseconds) developed in the latency between Schaffer collateral stimulation and the consequent CA3 field discharge. Eventually, no field responses could be evoked by Schaffer collateral stimulation in either areas CA1 and CA3. However, action potential discharge from CA1 pyramidal cells in response to Schaffer collateral stimulation could be evoked with little change in response latency. Indeed, for the entire duration of the experiments (greater than two hours), action potential discharges form CA1 pyramidal cells could be evoked at short latency by Schaffer collateral stimulation. Further, although stimulation-evoked hyperexcited discharges of CA3 were eventually blocked after prolonged exposure to low-$[Cl^-]_o$ medium, the antidromic response in CA3 appeared to be preserved.

EXAMPLE 6

Effects of Chloride-cotransport Antagonism on the Synchronization of Burst Discharges in CA1 Pyramidal Cells The foregoing data suggest the disappearance of the field responses may be due to a desynchronization of the occurrence of action potentials among neurons. That is, although synaptically-driven excitation of CA1 pyramidal cells was not preserved, action potential synchrony among the CA1 neuronal population was not sufficient to summate into a measurable DC field response. In order to test this, paired intracellular recordings of CA1 pyramidal cells were acquired simultaneously with CA1 field responses. In these experiments, both the intracellular electrodes and the field recording electrodes were placed within 200 μm of one another.

During the period of maximum spontaneous activity induced by bicuculline-containing low-$[Cl^-]_o$ medium, recordings showed that action potentials between pairs of CA1 neurons and the CA1 field discharges were tightly synchronized both during spontaneous and stimulation-evoked discharges. After continued exposure to low-$[Cl^-]_o$ medium, when the amplitude of the CA1 field discharge began to broaden and diminish, both spontaneous and stimulation-evoked discharges showed a desynchronization in the timing of the occurrences of action potentials between pairs of CA1 neurons, and between the action potentials and the field responses. This desynchronization was coincident with the suppression of CA1 field amplitude. By the time that spontaneous bursting in CA1 ceased, a significant increase in latency had developed between Schaffer collateral stimulation and CA1 field discharge. At this time, paired intracellular recordings showed a dramatic desynchronization in the timing of action potential discharge between pairs of neurons and between the occurrence of action potentials and the field discharges evoked by Schaffer collateral stimulation.

It is possible that the observed desynchronization of CA1 action potential discharge is due to the randomization of mechanisms necessary for synaptically-driven action potential generation, such as a disruption in the timing of synaptic release or random conduction failures at neuronal processes. If this were the case, then one would expect that the occurrence of action potentials between a given pair of neurons would vary randomly with respect to one another, from stimulation to stimulation. We tested this by comparing the patterns of action potential discharge of pairs of neurons between multiple consecutive stimuli of the Schaffer collaterals. During each stimulation event, the action potentials occurred at nearly identical times with respect to one another, and showed an almost identical burst morphology from stimulation to stimulation. We also checked to see whether the occurrence of action potentials between a given pair of neurons during spontaneous field discharges was fixed in time. The patterns of action potential discharges from a given pair of CA1 neurons was compared between consecutive spontaneous field bursts during the time when the occurrence of action potentials was clearly desynchronized. Just as in the case of stimulation-evoked action potential discharge described above, the action potentials generated during a spontaneous population discharge occurred at nearly identical times with respect to one another, and showed a nearly identical burst morphology from one spontaneous discharge to the next.

EXAMPLE 7

Effects of Low-chloride Treatment on Spontaneous Synaptic Activity

It is possible that the anti-epileptic effects associated with chloride-cotransport antagonism are mediated by some action on transmitter release. Blockade of chloride-cotransport could alter the amount or timing of transmitter released from terminals, thus affecting neuronal synchronization. To test whether low-$[Cl^-]_o$ exposure affected mechanisms associated with transmitter release, intracellular CA1 responses were recorded simultaneously with CA1 and CA3 field responses during a treatment which dramatically increases spontaneous synaptic release of transmitter from presynaptic terminals.

Increased spontaneous release of transmitter was induced by treatment with 4-AP (100 $\mu$M). After 40 minutes exposure to 4-AP-containing medium, spontaneous synchronized burst discharges were recorded in area CA1 and CA3. Switching to 4-AP-containing low-$[Cl^-]_o$ medium led initially, as was shown previously, to enhanced spontaneous bursting. High-grain intracellular recordings showed that high-amplitude spontaneous synaptic activity was elicited by 4-AP treatment. Further exposure to low-chloride medium blocked spontaneous burst discharge in CA1, although CA3 continued to discharge spontaneously. At this time, CA1 intracellular recordings showed that spontaneous synaptic noise was further increased, and remained so for prolonged exposure times to 4-AP-containing low-chloride medium. These data suggest that mechanisms responsible for synaptic release from terminals are not adversely affected by low-chloride exposure in a manner that could explain the blockade of 4-AP-induced spontaneous bursting in CA1. These results also eliminate the possibility that the effects of low-$[Cl^-]_o$ exposure are due to alterations in CA1 dendritic properties which would compromise their efficiency in conducting PSPs to the soma.

Experimental Methods for Examples 8 to 12

In all of the following experiments, $[Cl^-]_o$ was reduced by equimolar replacement of NaCl with Na$^+$-gluconate. Gluconate was used rather than other anion replacements for several reasons. First, patch-clamp studies have demonstrated that gluconate appears to be virtually impermeant to chloride channels, whereas other anions (including methylsulfate, sulfate, isethionate, and acetate) are permeable to varying degrees. Second, transport of extracellular potassium through glial Na$^+$, K$^+$, 2Cl cotransport is blocked when extracellular chloride is replaced by gluconate but is not completely blocked when replaced by isethionate. Since this furosemide-sensitive cotransporter plays a significant role in cell swelling and volume changes of the extracellular space (ECS), we wished to use the appropriate anion replacement so that the effects of our treatment would be comparable to previous furosemide experiments. [Hochman, D. W., Baraban, S. C., Owens, J. W. M., and Schwartzkroin, P. A., "Dissociation of synchronization and excitability in furosemide blockade of epileptiform activity." Science, Vol. 270, pp. 99–102 (1995), U.S. Pat. No. 5,902,732] Third, formate, acetate, and proprionate generate weak acids when employed as Cl$^-$ substitutes and lead to a prompt fall in intracellular pH; gluconate remains extracellular and has not been reported to induce intracellular pH shifts. Fourth, for purposes of comparison we wished to use the same anion replacement that had been used in previous studies examining the effects of low-$[Cl^-]_o$ on activity-evoked changes of the ECS.

There is some suggestion that certain anion-replacements might chelate calcium. Although subsequent work has failed to demonstrate any significant ability of anion-substitutes to chelate calcium, there is still some concern in the literature regarding this issue. Calcium chelation did not appear to be an issue in the following experiments, since resting membrane potentials remained normal and synaptic responses (indeed, hyperexcitable synaptic responses) could be elicited even after several hours of exposure to medium in which $[Cl^-]_o$ had been reduced by gluconate substitution. Further, we confirmed that calcium concentration in our low-$[Cl^-]_o$-medium was identical to that in our control-medium by measurements made with Ca$^{2++}$-selective microelectrodes.

Sprague-Dawley adult rats were prepared as previously described. Briefly, transverse hippocampal slices, 400 $\mu$m thick, were cut using a vibrating cutter. Slices typically contained the entire hippocampus and subiculum. After cutting, slices were stored in an oxygenated holding chamber for at least one hour prior to recording. All recordings were acquired in an interface type chamber with oxygenated (95%O2/5%CO2) artificial cerebral spinal fluid (ACSF) at 34°–35° C. Normal ACSF contained (in mmol/l): 124 NaCl, 3 KCl, 1.25 NaH2PO4, 1.2 MgSO4, 26 NaHCO3, 2 CaCl2, and 10 dextrose. In some experiments, normal or low-chloride medium was used containing bicuculline (20 $\mu$M), 4-AP (100 $\mu$M), or high-K$^+$ (12 mM). Low-chloride solutions (7, 16, and 21 mM $[Cl^-]_o$) were prepared by equimolar replacement of NaCl with Na$^+$-gluconate (Sigma Chemical Co., St. Louis, Mo.). All solutions were prepared so that they had a pH of approximately 7.4 and an osmolarity of 290–300 mOsm at 35° C. and at equilibrium from carboxygenation with 95%O2/5%CO2.

Sharp-electrodes filled with 4 M potassium acetate were used for intracellular recordings from CA1 pyramidal cells. Field recordings from the CA1 or CA3 cell body layers were acquired with low-resistance glass electrodes filled with NaCl (2 M). For stimulation of the Schaffer collateral pathway, a small monopolar electrode was placed on the surface of the slice midway between areas CA1 and CA3. Spontaneous and stimulation-evoked activities from field and intracellular recordings were digitized (Neurocorder, Neurodata Instruments, New York, N.Y.), and stored on video tape. AxoScope software (Axon Instruments Inc.) on a PC-computer was used for off-line analyses of data.

Ion-selective microelectrodes were fabricated according to standard methods well known in the art. Double-barreled pipettes were pulled and broken to a tip diameter of approximately 3.0 µm. The reference barrel was filled with ACSF and the other barrel was sylanized and the tip back-filled with a resin selective for $K^+$ (Corning 477317). The remainder of the sylanized barrel was filled with KCl (140 mM). Each barrel was led, via Ag/AgCl wires, to a high impedance dual-differential amplifier (WPI FD223). Each ion-selective microelectrode was calibrated by the use of solutions of known ionic composition and was considered suitable if it was characterized by a near-Nernstian slope response and if it remained stable throughout the duration of the experiment.

After placement in the interface chamber, slices were superfused at approximately 1 ml/minute. At this flow-rate, it took approximately 8–10 minutes for changes in perfusion media to be completed. All of the times reported here have taken this time-delay into account and have an error of approximately ±2 minutes.

EXAMPLE 8

Effects of Low-$[Cl^-]_o$ on CA1 Field Recordings

Other studies have shown that prolonged exposure of cortical and hippocampal slices to low-$[Cl^-]_o$ does not affect basic intrinsic and synaptic properties such as input resistance, resting membrane potential, depolarization-induced action-potential generation, or excitatory synaptic transmission. A previous study has also partly characterized the epileptogenic properties of low-$[Cl^-]_o$ exposure to CA1 area of hippocampus. The following studies were performed to observe the times of onset and possible cessation of low-$[Cl^-]_o$-induced hyperexcitability and hypersynchronization. Slices (n=6) were initially perfused with normal medium until stable intracellular and field recordings were established in a CA1 pyramidal cell and the CA1 cell body layer, respectively. In two experiments, the same cell was held throughout the entire length of the experiment (greater than 2 hours). In the remaining experiments (n=4), the initial intracellular recording was lost during the sequence of medium changes and additional recordings were acquired from different cells. Patterns of neuronal activity in these experiments were identical to those seen when a single cell was observed.

The field and intracellular electrodes were always placed in close proximity to one another (<200 µm). In each case, after approximately 15–20 minutes exposure to the low-$[Cl^-]_o$-medium (7 mM), spontaneous bursting developed, first at the cellular level, and then in the field. This spontaneous field activity, representing synchronized burst discharge in a large population of neurons, lasted from 5–10 minutes, after which time the field recording became silent. When the field first became silent, the cell continued to discharge spontaneously. This result suggests that population activity has been "desynchronized" while the ability of individual cells to discharge has not been impaired. After approximately 30 minutes exposure to low-$[Cl^-]_o$-medium, intracellular recording showed that cells continued to discharge spontaneously even though the field remained silent. The response of the cell to intracellular current injection at two time points demonstrated that the cell's ability to generate action potentials had not been impaired by low-$[Cl^-]_o$ exposure. Further, electrical stimulation in CA1 stratum radiatum elicited burst discharges, indicating that a hyperexcitable state was maintained in the tissue.

EXAMPLE 9

Effects of Low-$[Cl^-]_o$ on High-$[K^+]_o$-induced Epileptiform Activity in CA1

The previous set of experiments showed that tissue exposure to low-$[Cl^-]_o$ medium induced a brief period of spontaneous field potential bursting which ceased within 10 minutes. If a reduction of $[Cl^-]_o$ is indeed eventually capable of blocking spontaneous epileptiform (i.e. synchronized) bursting, then these results suggest that anti-epileptic effects would likely be observable only after this initial period of bursting activity has ceased. We therefore examined the temporal effects of low-$[Cl^-]_o$-treatment on high-$[K^+]_o$-induced bursting activity. Slices (n=12) were exposed to medium in which $[K^+]_o$ had been increased to 12 mM, and field potentials were recorded with a field electrode in the CA1 cell body layer. Spontaneous field potential bursting was observed for at least 20 minutes, and then the slices were exposed to medium in which $[K^+]_o$ was maintained at 12 mM, but $[Cl^-]_o$ was reduced to 21 mM. Within 15–20 minutes after the tissue was exposed to the low-$[Cl^-]_o$/high-$[K^+]_o$-medium, the burst amplitude increased and each field event had a longer duration. After a brief period of this facilitated field activity (lasting 5–10 minutes), the bursting stopped. To test whether this blockade was reversible, after at least 10 minutes of field potential silence, we switched back to high-$[K^+]_o$-medium with normal $[Cl^-]_o$. The bursting returned within 20–40 minutes. Throughout each experiment, the CA1 field response to Schaffer collateral stimulation was monitored. The largest field responses were recorded just before the cessation of spontaneous bursting, during the period when the spontaneous bursts had the largest amplitude. Even after the blockade of spontaneous bursting, however, multiple population spikes were elicited by Schaffer collateral stimulation, indicating that synaptic transmission was intact, and that the tissue remained hyperexcitable.

In four slices, intracellular recordings from CA1 pyramidal cells were acquired along with the CA1 field recording. During the period of high-$[K^+]_o$-induced spontaneous bursting, hyperpolarizing current was injected into the cell so that postsynaptic potentials (PSPs) could be better observed. After low-$[Cl^-]_o$-blockade of spontaneous bursting, spontaneously occurring action potentials and PSPs were still observed. These observations further support the view that synaptic activity, per se, was not blocked by the low-$[Cl^-]_o$ treatment.

EXAMPLE 10

Low-$[Cl^-]_o$-blockade of Epileptiform Activity Induced by 4-AP, high-$[K^+]_o$, and Bicuculline in CA1 and CA3

We next tested whether low-$[Cl^-]_o$ treatment could block epileptiform activity in areas CA1 and CA3, which was elicited by different pharmacological treatments, as we had shown for furosemide treatment. For this set of experiments, we chose to test the effects of low-$[Cl^-]_o$ treatment on spontaneous bursting which had been induced by high-$[K^+]_o$ (12 mM) (n=5), 4-AP (100 $\mu$M) (n=4), and bicuculline (20 and 100 $\mu$M) (n=5). In each set of experiments, field responses were recorded simultaneously from areas CA1 and CA3, and in each case, the spontaneous epileptiform activity in both areas CA1 and CA3, was reversibly blocked within 30 minutes after $[Cl^-]_o$ in the perfusion medium had been reduced to 21 mM. These data suggest that, like furosemide, low-$[Cl^-]_o$ reversibly blocks spontaneous bursting in several of the most commonly studied in vitro models of epileptiform activity.

EXAMPLE 11

Comparison Between Low-$[Cl^-]_o$ and Furosemide on Blockade of High-$[K^+]_o$-induced Epileptiform Activity The data from the previous sets of experiments are consistent with the hypothesis that the anti-epileptic effects of both low-$[Cl^-]_o$ and furosemide are mediated by their actions on the same physiological mechanisms. To further test this hypothesis, we compared the temporal sequence of effects of low-$[Cl^-]_o$ (n=12) and furosemide (2.5 and 5 mM) (n=4) on high-$[K^+]_o$-induced bursting, as recorded with a field electrode in CA1. We found that both low-$[Cl^-]_o$ and furosemide treatment induced a similar temporal sequence of effects: an initial brief period of increased amplitude of field activity, and then blockade (reversible) of spontaneous field activity. In both cases, electrical stimulation of the Schaffer collaterals elicited hyperexcited responses even after the spontaneous bursting had been blocked.

EXAMPLE 12

Consequences of Prolonged Exposure to Low-$[Cl^-]_o$ Medium with Varied $[K^+]_o$ In the preceding experiments, we monitored field activity in some slices for >1 hour after the spontaneous bursting had been blocked by low-$[Cl^-]_o$ exposure. After such prolonged low-$[Cl^-]_o$ exposure, spontaneous, long-lasting, depolarizing shifts developed. The morphology and frequency of these late-occurring field events appeared to be related to the extracellular potassium and chloride concentrations. Motivated by these observations, we performed a set of experiments in which we systematically varied $[Cl^-]_o$ and $[K^+]_o$ and observed the effects of these ion changes on the late-occurring spontaneous field events.

In our first set of experiments, slices were exposed to medium containing low-$[Cl^-]_o$ (7 mM) and normal-$[K^+]_o$ (3 mM) (n=6). After 50–70 minutes exposure to this medium, spontaneous events were recorded in area CA1; these events appeared as 5–10 mV negative shifts in the DC field, with the first episode lasting for 30–60 seconds. Each subsequent episode was longer than the previous one. This observation suggested that ion-homeostatic mechanisms were diminished over time as a result of the ion concentrations in the bathing medium. In some experiments (n=2) in which these negative DC field shifts had been induced, intracellular recordings from CA1 pyramidal cells were acquired simultaneously with the CA1 field recordings.

For these experiments, the intracellular and field recordings were acquired close to one another (<200 $\mu$m). Prior to each negative field shift (10–20 seconds), the neuron began to depolarize. Cellular depolarization was indicated by a decrease in resting membrane potential, an increase in spontaneous firing frequency, and a reduction of action potential amplitude. Coincident with the onset of the negative field shifts, the cells became sufficiently depolarized so that they were unable to fire spontaneous or current-elicited (not shown) action potentials. Since neuronal depolarization began 10–20 seconds prior to the field shift, it may be that a gradual increase in extracellular potassium resulted in the depolarization of a neuronal population, thus initiating these field events. Such an increase in $[K^+]_o$ might be due to alterations of the chloride-dependent glial cotransport mechanisms that normally move potassium from extracellular to intracellular spaces. To test whether increases in $[K^+]_o$ preceded these negative field shifts (and paralleled cellular depolarization), experiments (n=2) were performed in which a $K^+$-selective microelectrode was used to record changes in $[K^+]_o$.

In each experiment, the $K^+$-selective microelectrode and a field electrode were placed in the CA1 pyramidal layer close to one another (<200 $\mu$m), and a stimulation pulse was delivered to the Schaffer collaterals every 20 seconds so that the magnitude of the population spike could be monitored. Multiple spontaneously occurring negative field shifts were evoked by perfusion with low-$[Cl^-_o]$ (7 mM) medium. Each event was associated with a significant increase in, $[K^+]_o$, with the $[K^+]_o$ increase starting several seconds prior to the onset of negative field shift. A slow 1.5–2.0 mM increase in $[K^+]_o$ occurred over a time interval of approximately 1–2 minute seconds prior to the onset of each event. The stimulation-evoked field responses slowly increased in amplitude over time, along with the increasing $[K^+]_o$, until just before the negative field shift.

In a second set of experiments (n=4), $[K^+]_o$ was increased to 12 mM and $[Cl^-]_o$ was increased to 16 mM. After 50–90 minutes exposure to this medium, slow, oscillations were recorded in area CA1. These oscillations were characterized by 5–10 mV negative DC shifts in the field potential and had a periodicity of approximately 1 cycle/40 seconds. Initially, these oscillations occurred intermittently and had an irregular morphology. Over time, these oscillations became continuous and developed a regular waveform. Upon exposure to furosemide (2.5 mM), the amplitude of the oscillations was gradually decreased and the frequency increased until the oscillations were completely blocked. Such low-$[Cl]_o$-induced oscillations in tissue slices have not been previously reported. However, the temporal characteristics of the oscillatory events bear a striking resemblance to the low-$[Cl]_o$ induced $[K^+]_o$ oscillations which were previously described in a purely axonal preparation.

In a third set of experiments (n=5) $[Cl^-]_o$ was further increased to 21 mM and $[K^+]_o$ was reduced back to 3 mM. In these experiments, single, infrequently occurring negative shifts of the field potential developed within 40–70 minutes (data not shown). These events (5–10 mV) lasting 40–60 seconds, occurred at random intervals, and maintained a relatively constant duration throughout the experiment. These events could sometimes be elicited by a single electrical stimulus delivered to the Schaffer collaterals.

Finally, in a final set of experiments (n=5), $[Cl^-]_o$ was kept at 21 mM and $[K^+]_o$ was raised to 12 mM. In these experiments, late-occurring spontaneous field events were not observed during the course of the experiments (2–3 hours).

EXAMPLE 13

Changes in $[K^+]_0$ During Low-chloride Exposure

Sprague-Dawley adult rats were prepared as previously described. Transverse hippocampal slices, 400 $\mu$m thick, were cut with a vibrating cuter and stored in an oxygenated holding chamber for 1 hour before recording. A submersion-type chamber was used for $K^+$-selective microelectrode recordings. Slices were perfused with oxygenated (95% $O_2$–5% $CO_2$) artificial cerebrospinal fluid (ACSF) at 34–35° C. Normal ACSF contained 10 mM dextrose, 124 mM NaCl 3 mM KCl, 1.25 mM $NaH_2PO_4$, 1.2 mM $MgSO_4$, 26 mM $NaHCO_3$ and 2 mM $CaCl_2$. In some experiments, normal or low-chloride medium was used containing 4-aminopyridine (4-AP) at 100 μM. Low-chloride solutions (21 mM $[Cl]_o$) were prepared by equimolar replacement of NaCl with Na+-gluconate (Sigma Chemical Co.).

Field recordings from the CA1 or CA3 cell body layers were acquired with low-resistance glass electrodes filled with NaCl (2M). For stimulation of the Schaffer collateral pathway, a monopolar stainless-steel electrode was placed on the surface of the slide midway between areas CA1 and CA3. All recordings were digitized (Neurorocorder, Neurodata Instruments, New York, N.Y.) and stored on videotape.

$K^+$ selective microelectrodes were fabricated according to standard methods. Briefly, the reference barrel of a double-barreled pipette was filled with ACSF, and the other barrel was sylanized and the tip back-filled with KCl with $K^+$-selective resin (Corning 477317). Ion-selective microelectrodes were calibrated and considered suitable if they had a Nernstian slope response and remained stable throughout the duration of the experiment.

Exposure of hippocampal slices to low-$[Cl-]_0$ medium has been shown to include a temporally-dependent sequence of changes on the activity of CA1 pyramidal cells, with three characteristics phases, as described above. In brief, exposure to low-$[Cl-]_0$ medium results in a brief period of increased hyperexcitability and spontaneous epileptiform discharge. With further exposure to low-$[Cl^-]_0$ medium, spontaneous epileptiform activity is blocked, but cellular hyperexcitability remains, and action potential firing times become less synchronized with one another. Lastly, with prolonged exposure, the action potential firing times become sufficiently desynchronized so that stimulation-evoked field responses completely disappear, yet individual cells continue to show monosynaptically-evoked responses to Schaffer collateral stimulation. The following results demonstrate that the antiepileptic effects of furosemide on chloride-cotransport antagonism are independent of direct actions on excitatory synaptic transmission, and are a consequence of a desynchronization of population activity with our any associated decrease in excitability.

In six hippocampal slices, $K^+$-selective and field microelectrodes were placed in the CA1 cell body layer, and a stimulating electrode was placed on the Schaffer collateral pathway, and single-pulse stimuli (300 μs) were delivered every 20 seconds (FIG. 19). After stable baseline $[K^+]_0$ was observed for at least 20 minutes, the perfusion was switched to low-$[Cl^-]_0$ medium. Within 1–2 minutes of exposure to low-$[Cl^-]_0$ medium, the field responses became hyperexcitable as the $[K^+]_0$ began to rise. After approximately 4–5 minutes of exposure to low-$[C^-]_0$ medium the magnitude of the field response diminished, until it was completely abolished. The corresponding recording of ($[K^+]_0$) showed that potassium began to rise immediately after exposure to low-$[Cl^-]_0$ medium, and that the peak of this $[K^+]_0$ rise corresponded in time to the maximally hyperexcitable CA1 field response. Coincident with the reduction of the magnitude of the field response, the $[K^+]_0$ began to diminish until after 8–10 minutes exposure to low-$[Cl^-]_0$ medium, it became constant for the remainder of the experiment at 1.8–2.5 mM above control levels. Four slices were switched back to control medium and allowed to fully recover. The experiment was then repeated with the $K^+$-selective microelectrode placed in the stratum radiatum. A similar sequence of changes in $[K^+]_0$ was observed in the dendritic layer, with the values of $[K^+]_0$ being 0.2–0.3 mM less than those observed in the cell body layers.

In four hippocampal slices, the responses of stimulation-evoked changes in $[K^+]_0$ between control conditions and after the CA1 field response was completely abolished by low-$[Cl^-]_0$ exposure were compared. In each slice, the $[K^+]_0$-selective measurements were acquired first in the cell body layer, and then after allowance for complete recovery in control medium, the experiment was repeated with the $K^+$-selective electrode moved to the stratum radiatum. Each stimulation trial consisted of a 10 Hz volley delivered to the Schaffer collateral for 5 seconds. The peak rises in $[K^+]_0$ were similar between control conditions an after prolonged exposure to low-$[Cl^-]_0$ medium, and between the cell body and dendritic layers. However, the recovery times observed after prolonged exposure to low-$[Cl^-]_0$ were significantly longer than those observed during control conditions.

These results demonstrate that the administration of furosemide resulted in increased $[K^+]_0$ in the extracellular spaces. Exposure of the brain tissue to low-$[Cl^-]_0$ medium immediately induced a rise in $[K^+]_0$ by 1–2 mM, which remained throughout the duration of exposure, and was coincident with the initial increase in excitability and the eventual abolishment of the CA1 field response. This loss of CA1 field response during low-$[Cl^-]_0$ exposure is most likely due to the desynchronization of neuronal firing times. Significantly, the stimulation-evoked increases in $[K^+]_0$, in both the cell body and dendritic layers were nearly identical before and after the complete low-$[Cl^-]_0$ blockade of the CA1 field response. This data suggests that comparable stimulation-evoked synaptic drive and action potential generation occurred under control conditions and after low-$[Cl^-]_0$ blockade of the field. Together these data demonstrate that the antiepileptic and desynchronizing effects of the chloride-cotransport antagonist, furosemide, are independent of direct actions on excitatory synaptic transmission and are a consequence of a desynchronization of population activity without decrease in excitability.

EXAMPLE 14

Changes in Extracellular pH During Low-chloride Exposure

Antagonists of the anion/chloride-dependent cotransporter, such as furosemide and low-$[Cl^-]_0$, may affect extracellular pH transients that might contribute to the maintenance of synchronized population activity. Rat hippocampal brain slices were prepared as described in Example 13, except the $NaHCO_3$ was substituted by equimolar amount of HEPES (26 nM) and an interface-type chamber was used.

In four hippocampal brain slices continuous spontaneous bursting was elicited by exposure to medium containing 100 μM 4-AP, as described in Example 13 . Field recordings were acquired simultaneously from the cell body layers in areas CA1 and CA3. A stimulus delivered every 30 seconds to the Schaffer collaterals throughout the duration of the experiments. After at least 20 minutes of continuous bursting was observed, the slices were exposed to nominally bicarbonate free, 4-AP-containing HEPES medium. There were no significant changes observed in the spontaneous or stimulation-evoked field responses resulting from prolonged exposure (0.2 hours) to HEPES medium. After the slices had been exposed for at least 2 hours to the HEPES medium, the perfusion was switched to 4-AP-containing HEPES medium in which the $[Cl^-]_0$ had been reduced to 21 mM. Exposure to the low-$[Cl^-]_0$ HEPES medium induced the identical sequences of events, and at the same time course, as had previously been observed with low-$[Cl^-]_0$ NaHCO$_3$-containing medium. After complete blockade of spontaneous bursting, the perfusion medium was switched back HEPES medium with normal $[Cl^-]_0$. Within 20–40 minutes, spontaneous bursting resumed. At the time the spontaneous bursting had resumed, the slices had been perfused with nominally bicarbonate-free HEPES medium for greater than 3 hours.

This data suggests that the actions of chloride-cotransport antagonism on synchronization and excitability are independent of affects on the dynamics of extracellular pH.

FIG. 4 illustrates a schematic model of ion cotransport under conditions of reduced $[Cl^-]$. FIG. 4A, left panel, shows that the chloride gradient necessary for the generation of IPSPs in neurons is maintained by efflux of ions through a furosemide-sensitive K$^+$, Cl$^-$ cotransporter. Under normal conditions, a high concentration of intracellular potassium (maintained by the 3Na$^+$, 2K$^+$-ATPase pump) serves as the driving force for the extrusion of Cl$^-$ against its concentration gradient. In glial cells, as shown in the right panel of FIG. 4A, the movement of ions through the furosemide-sensitive Na$^+$, K$^+$, 2Cl$^-$-cotransporter is from extracellular to intracellular spaces. The ion-gradients necessary for this cotransport are maintained, in part, by the "transmembrane sodium cycle": sodium ions taken into glial cells through Na$^+$, K$^+$, 2Cl$^-$-cotransport are continuously extruded by the 3Na$^+$, 2K$^+$,-ATPase pump so that a low intracellular sodium concentration is maintained. The rate and direction of ion-flux through the furosemide-dependent cotransporters are functionally proportional to their ion-product differences written as $[K^+]_i \times [Cl^-]_i - [K^+]_o \times [Cl^-]_o$) for neuronal K$^+$, Cl$^-$ cotransport and as $[Na^+]_i \times [K^+]_i \times [Cl^-]^2_i - [Na^+]_o \times [K^+]_o \times [Cl^-]^2_o$) for glial NA$^+$, K$^+$, 2Cl$^-$ cotransport. The sign of these ion-product differences show the direction of ion transport with positive being from intracellular to extracellular spaces.

Figure 4B:
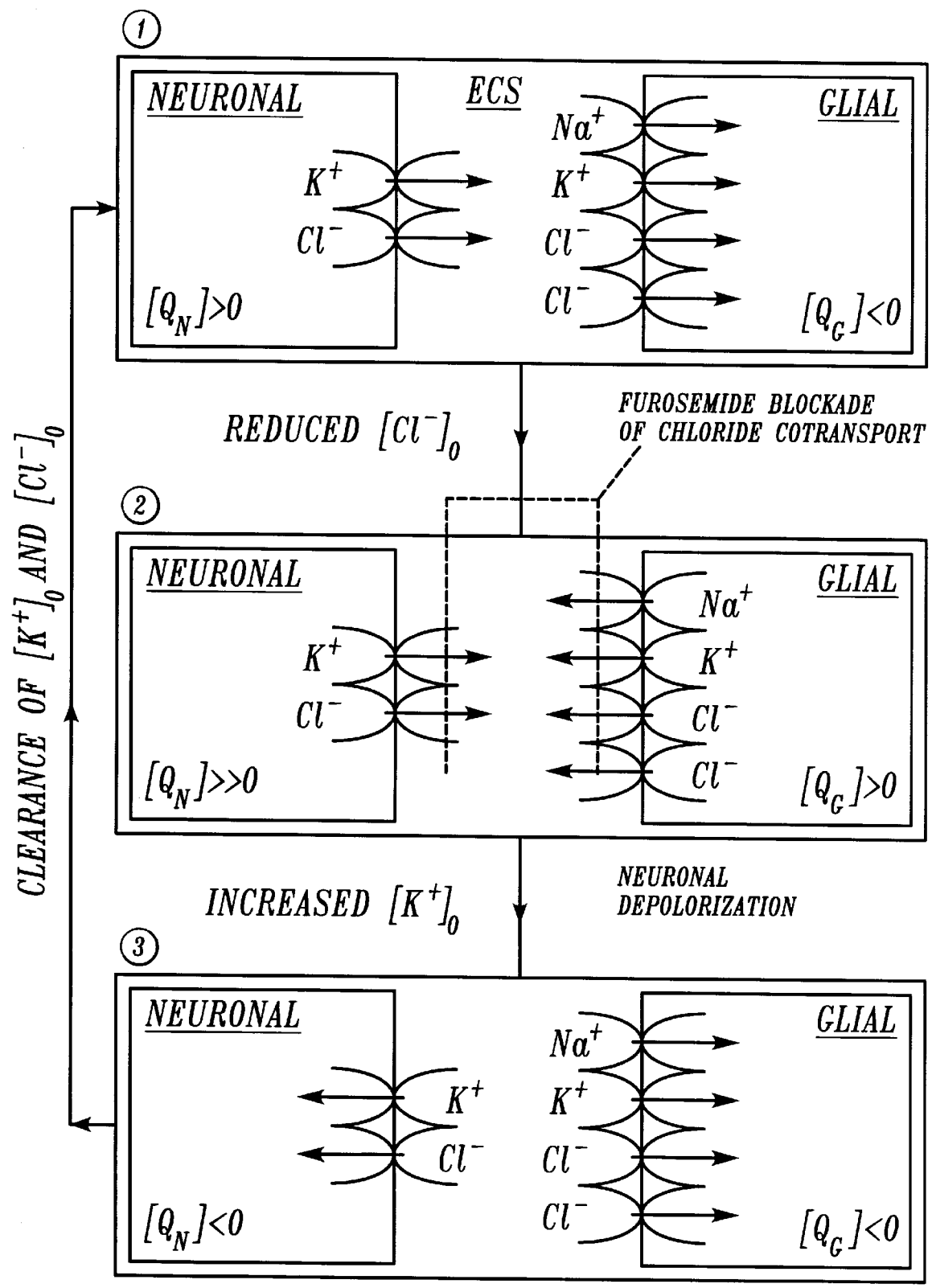

FIG. 4B shows a schematic phenomenological model that explains the emergence of the late-occurring spontaneous field events that arise as a result of prolonged low -$[Cl^-]_o$ exposure. We denote the ion-product differences for neurons and glia as Q$_N$ and Q$_G$, respectively. Under control conditions (1), the differences of the ion-products for neurons are such that K$^+$ and Cl$^-$ are cotransported from intracellular to extracellular spaces (Q$_N$>0); the differences in ion-products for glial cells are such that Na$^+$, K$^+$ and Cl$^-$ are cotransported from the ECS to intracellular compartments (Q$_G$<0). When $[Cl^-]_o$ is reduced (2), the ion-product differences are altered so that neuronal efflux of KCl is increased however, the glial ion cotransport is reversed (Q$_G$>0), so that there is a net efflux of KCl and NaCl from intracellular to extracellular spaces. These changes result in buildup of extracellular potassium over time. Eventually, $[K^+]_o$ reaches a level that induces the depolarization of neuronal populations, resulting in an even larger accumulation of $[K^+]_o$. This large accumulation of extracellular ions then serves to reverse the ion-product differences so that KCl is moved from extracellular to intracellular spaces (Q$_N$<0, Q$_G$<0) (3). Further clearance of th extracellular potassium eventually resets the transmembrane ion gradients to initial conditions. By cycling through this process, repetitive negative field events are generated.

What is claimed is:

1. A method for treating a condition of the central nervous system in a mammalian subject in need thereof comprising delivering an effective amount of a treatment composition comprising a Na$^+$K$^+$Cl$^-$ cotransporter antagonist to the subject's central nervous system, wherein the condition is selected from the group consisting of seizures, seizure disorders, epilepsy and status epilepticus, and wherein the treatment composition has higher activity as a glial cell ion-dependent cotransporter antagonist than as a neuronal cell ion-dependent cotransporter antagonist.

2. A method for treating a condition of the central nervous system selected from the group consisting of seizures, seizure disorders, epilepsy and status epilepticus in a mammalian subject in need thereof, consisting essentially of delivering an effective amount of a loop diuretic to the central nervous system, wherein the loop diuretic has higher activity in a central nervous system cell population than in a renal cell population.

3. A method for treating a condition of the central nervous system selected from the group consisting of seizures, seizure disorders, epilepsy and status epilepticus in a mammalian subject in need thereof, consisting essentially of delivering an effective amount of a Na$^+$K$^+$Cl$^-$ antagonist to the central nervous system.

4. A method for treating a condition of the central nervous system in a mammalian subject in need thereof comprising delivering an effective amount of a treatment composition comprising a loop diuretic to the subject's central nervous system, wherein the condition is selected from the group consisting of seizures, seizure disorders, epilepsy and stanza epilepticus, and wherein the treatment composition has higher activity as a glial cell iondependent cotransporter antagonist than as a neuronal cell ion-dependent cotransporter antagonist.

5. The method of claim 1, wherein the Na$^+$K$^+$Cl$^-$ cotransporter antagonist is delivered to the central nervous system by one or more of the following: intracranial administration, local intracerebral administration, administration into the cerebral spinal fluid, administration in a sustained release formulation, or formulated to facilitate crossing of the blood brain barrier.

6. The method of claim 4, wherein the loop diuretic is delivered to the central nervous system by one or more of the following: intracranial administration, local intracerebral administration, administration into the cerebral spinal fluid, administration in a sustained release formulation, or formulated to facilitate crossing of the blood brain barrier.

* * * * *

UNITED STATES PATENT AND TRADEMARK OFFICE
CERTIFICATE OF CORRECTION

PATENT NO. : 6,495,601 B1
DATED : December 17, 2002
INVENTOR(S) : Daryl W. Hochman It is certified that error appears in the above-identified patent and that said Letters Patent is hereby corrected as shown below:

<u>Column 46,</u>
Line 40, replace "epilepsy and stanza" with -- epilepsy and status --

Signed and Sealed this

Fourteenth Day of October, 2003

JAMES E. ROGAN
*Director of the United States Patent and Trademark Office*